US007732579B2

(12) United States Patent
Stanker et al.

(10) Patent No.: US 7,732,579 B2
(45) Date of Patent: Jun. 8, 2010

(54) HIGH-AFFINITY MONOCLONAL ANTIBODIES FOR BOTULINUM TOXIN TYPE A

(75) Inventors: Larry H Stanker, Livermore, CA (US); Luisa W Cheng, San Francisco, CA (US); Miles C Scotcher, Castro Valley, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/138,415

(22) Filed: Jun. 13, 2008

(65) Prior Publication Data

US 2009/0117587 A1 May 7, 2009

Related U.S. Application Data

(60) Provisional application No. 60/934,530, filed on Jun. 13, 2007.

(51) Int. Cl.
*C07K 16/12* (2006.01)
(52) U.S. Cl. .................. 530/388.4; 530/413; 435/7.1
(58) Field of Classification Search ............... None
See application file for complete search history.

(56) References Cited

U.S. PATENT DOCUMENTS

| 5,932,449 | A | 8/1999 | Emanuel et al. |
| 6,667,158 | B1 | 12/2003 | Bavari et al. |
| 7,049,085 | B2 | 5/2006 | Bavari et al. |
| 7,341,843 | B2 * | 3/2008 | Atassi .................. 435/7.32 |
| 2002/0155114 | A1 | 10/2002 | Marks et al. |
| 2004/0175385 | A1 * | 9/2004 | Marks et al. ............. 424/164.1 |
| 2005/0042775 | A1 * | 2/2005 | Pomato et al. ............. 436/547 |
| 2008/0124328 | A1 * | 5/2008 | Marks et al. ............. 424/135.1 |

OTHER PUBLICATIONS

Bobrovnik, S.A., "Determination of antibody affinity by Elisa. Theory" J. Biochem. Biophys. Methods (2003) 57:213-236.
Friguet, B., A.F. Chaffotte, L. Djavadi-Ohaniance and M.E. Goldberg, "Measurements of the True Affinity Constant in Solution of Antigen-Antibody Complexes by Enzyme-Linked Immunosorbent Assay" J. of Immunological Methods (1985) 77:305-319.
Gill, D. M, "Bacterial Toxins: a Table of Lethal Amounts" Microbiological Reviews (1982) 46(1):86-94.
Sugasawara, R.J., B.E. Cahoon, and A.E. Karu, "The Influence of Murine Macrophage-Conditioned Medium on Cloning Efficiency, Antibody Synthesis, and Growth Rate of Hybridomas" J. Of Immunological Methods (1985) 79:263-275.
Turton, K., J.A. Chaddock, and K.R. Acharya, "Botulinum and tetanus neurotoxins: structure, function and therapeutic utility" Trends in Biochemcial Sciences (2002) 27(11):552-558.
Garcia-Rodriguez, C., R. Levy, J.W. Arndt, C.M. Forsyth, A. Razai, J. Lou, I. Geren, R.C. Stevens, and J.D. Marks, "Molecular evolution of antibody cross-reactivity got two subtypes of type A botulinum neurotoxin" Nature Biotechnology (2007) 25(1):107-116.

* cited by examiner

*Primary Examiner*—Robert B Mondesi
*Assistant Examiner*—Ginny Portner
(74) *Attorney, Agent, or Firm*—Howard V. Owens; John D. Fado; Leslie Shaw

(57) ABSTRACT

High affinity antibodies for binding epitopes of BoNT/A and hybridomas that produce such antibodies are described. The antibodies may be used in a kit for detecting BoNT/A in a sample.

10 Claims, 19 Drawing Sheets

FIG. 14

Mutagenesis

| Vector      | Light chain, from T-125 to Q-162                |              |
|-------------|-------------------------------------------------|--------------|
| pGS-Lc      | TELKVIDTNCINVIQPDGSYRSEELNLVIIGPSADIIQ          | SEQ ID NO:30 |
| pGS-LcΔ     | TELKVIDTN---------------LNLVIIGPSADIIQ          | SEQ ID NO:31 |
| pGS-Lc-QPD  | TELKVIDTNCINVIGGGGSYRSEELNLVIIGPSADIIQ          | SEQ ID NO:32 |
| pGS-Lc-RS   | TELKVIDTNCINVIQPDGSYGGEELNLVIIGPSADIIQ          | SEQ ID NO:33 |

A. Silver Stained

B. Anti-BoNt Commercial Antisera Western blot

C. Mab F1-40 Western blot

FIG. 19

SEQUENCE LISTING

<160> NUMBER OF SEQ ID NOS: 41

<210> SEQ ID NO 1
<211> LENGTH: 137
<212> TYPE: PRT
<213> ORGANISM: Clostridium botulinum

<400> SEQUENCE: 1

Met Ala Val Leu Gly Leu Leu Phe Cys Leu Leu Thr Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Leu Ser Leu
        35                  40                  45

Thr Asn Tyr Gly Val Ser Trp Val Arg Gln Pro Pro Lys Gly Leu
    50                  55                  60

Glu Trp Leu Gly Ile Ile Trp Gly Asp Gly Ser Thr Ser Tyr His Ser
65                  70                  75                  80

Ala Leu Thr Ser Arg Leu Ser Ile Ser Lys Asp Asn Ser Lys Ser Gln
                85                  90                  95

Val Phe Leu Thr Leu Asn Ser Leu Gln Thr Asp Asp Thr Ala Thr Tyr
            100                 105                 110

Tyr Cys Ala Thr Ala Tyr Tyr Gly Tyr Thr Leu Phe Ala Tyr Trp Gly
        115                 120                 125

Gln Gly Thr Leu Val Thr Val Ser Ala
    130                 135

<210> SEQ ID NO 2
<211> LENGTH: 139
<212> TYPE: PRT
<213> ORGANISM: Clostridium botulinum

<400> SEQUENCE: 2

Met Glu Ser Gln Thr Gln Val Phe Val Phe Val Leu Trp Leu Ser
1               5                   10                  15

Gly Val Asp Gly Met Glu Ser Gln Thr Gln Val Phe Val Phe Val Phe
            20                  25                  30

Leu Trp Leu Ser Gly Val Asp Gly Lys Phe Met Ser Thr Ser Val Gly
        35                  40                  45

Asp Arg Val Ser Ile Thr Cys Lys Ala Ser Gln Asp Val Ser Thr Thr
    50                  55                  60

Val Ala Trp Tyr Gln Gln Lys Pro Gly Gln Ser Pro Lys Leu Leu Ile
65                  70                  75                  80

```
Tyr Ser Ala Ser Tyr Arg Tyr Thr Gly Val Pro Asp Arg Phe Thr Gly
                85                  90                  95

Ser Gly Ser Gly Thr Asp Phe Thr Phe Thr Ile Ser Ser Val Gln Ala
            100                 105                 110

Glu Asp Leu Ala Val Tyr Tyr Cys Gln Gln His Tyr Ser Thr Pro Pro
        115                 120                 125

Thr Phe Gly Gly Gly Thr Lys Leu Glu Ile Lys
    130                 135
```

<210> SEQ ID NO 3
<211> LENGTH: 139
<212> TYPE: PRT
<213> ORGANISM: Clostridium botulinum

<400> SEQUENCE: 3

```
Met Glu Ser Gln Thr Gln Val Phe Val Phe Val Phe Leu Trp Leu Ser
1               5                   10                  15

Gly Val Asp Gly Asp Ile Val Met Thr Gln Phe Ala Gly Val Asp Gly
            20                  25                  30

Asp Ile Val Met Thr Gln Ser His Lys Phe Met Ser Thr Ser Val Gly
            35                  40                  45

Asp Arg Val Ser Ile Thr Cys Lys Ala Ser Gln Asp Val Ser Thr Thr
        50                  55                  60

Val Ala Trp Tyr Gln Gln Lys Pro Gly Gln Ser Pro Lys Leu Leu Ile
65                  70                  75                  80

Tyr Ser Ala Ser Tyr Arg Tyr Thr Gly Val Pro Asp Arg Phe Thr Gly
                85                  90                  95

Ser Gly Ser Gly Gln Gln His Tyr Ser Thr Pro Pro Thr Phe Gly Gly
            100                 105                 110

Gly Thr Lys Leu Glu Ile Lys Thr Asp Phe Thr Phe Thr Ile Ser Ser
        115                 120                 125

Val Gln Ala Glu Asp Leu Ala Val Tyr Tyr Cys
    130                 135
```

<210> SEQ ID NO 4
<211> LENGTH: 142
<212> TYPE: PRT
<213> ORGANISM: Clostridium botulinum

<400> SEQUENCE: 4

```
Met Asn Phe Gly Leu Ser Leu Val Phe Leu Val Leu Val Leu Lys Gly
1               5                   10                  15

Val Gln Cys Glu Val Met Leu Val Glu Ser Gly Gly Gly Leu Val Lys
            20                  25                  30

Pro Gly Gly Ser Leu Glu Leu Ser Cys Ile Ala Ser Gly Phe Thr Phe
        35                  40                  45

Ser Ser Tyr Ala Met Ser Trp Val Arg Gln Thr Pro Glu Lys Arg Leu
    50                  55                  60

Glu Trp Val Ala Ala Ile Asp Ser Gly Gly Tyr Tyr Thr Tyr Tyr Pro
65                  70                  75                  80

Asp Asn Val Lys Gly Arg Phe Thr Ile Ser Arg Asp Asn Ala Lys Asn
                85                  90                  95

Thr Leu Tyr Leu Gln Met Asn Ser Leu Arg Ser Glu Asp Thr Ala Ile
            100                 105                 110

Tyr Tyr Cys Thr Arg Gln Gly Thr Arg Val Ser Tyr Arg Tyr Val Leu
        115                 120                 125
```

```
Asp Tyr Trp Gly Gln Gly Thr Thr Leu Ser Val Ser Ser Ala
    130                 135                 140
```

```
<210> SEQ ID NO 5
<211> LENGTH: 108
<212> TYPE: PRT
<213> ORGANISM: Clostridium botulinum
<220> FEATURE:
<221> NAME/KEY: misc_feature
<222> LOCATION: (54)..(54)
<223> OTHER INFORMATION: X = Y/S
<220> FEATURE:
<221> NAME/KEY: misc_feature
<222> LOCATION: (56)..(56)
<223> OTHER INFORMATION: X = Y/S
<220> FEATURE:
<221> NAME/KEY: misc_feature
<222> LOCATION: (94)..(94)
<223> OTHER INFORMATION: X = S/T
<220> FEATURE:
<221> NAME/KEY: misc_feature
<222> LOCATION: (97)..(97)
<223> OTHER INFORMATION: X = P/L

<400> SEQUENCE: 5

Gly Asp Ile Val Met Thr Gln Ser His Lys Phe Met Ser Thr Ser Val
1               5                   10                  15

Gly Asp Arg Val Ser Ile Thr Cys Lys Ala Ser Gln Asp Val Ser Thr
            20                  25                  30

Thr Val Ala Trp Tyr Gln Gln Lys Pro Gly Gln Ser Pro Lys Leu Leu
        35                  40                  45

Ile Tyr Ser Ala Ser Xaa Arg Xaa Thr Gly Val Pro Asp Arg Phe Thr
50                  55                  60

Gly Ser Gly Ser Gly Thr Asp Phe Thr Phe Thr Ile Ser Ser Val Gln
65                  70                  75                  80

Ala Glu Asp Leu Ala Val Tyr Tyr Cys Gln Gln His Tyr Xaa Thr Pro
                85                  90                  95

Xaa Thr Phe Gly Gly Gly Thr Lys Leu Glu Ile Lys
            100                 105
```

```
<210> SEQ ID NO 6
<211> LENGTH: 40
<212> TYPE: PRT
<213> ORGANISM: Clostridium botulinum

<400> SEQUENCE: 6

Gly Gly Ala Thr Cys Cys Ala Thr Gly Cys Cys Ala Thr Thr Thr Gly
1               5                   10                  15

Thr Thr Ala Ala Thr Ala Ala Ala Cys Ala Ala Thr Thr Ala Ala Ala
            20                  25                  30

Thr Thr Ala Thr Ala Ala Ala Gly
        35                  40
```

```
<210> SEQ ID NO 7
<211> LENGTH: 35
<212> TYPE: PRT
<213> ORGANISM: Clostridium botulinum

<400> SEQUENCE: 7

Cys Thr Cys Gly Ala Gly Thr Thr Ala Thr Thr Thr Ala Gly Ala Ala
1               5                   10                  15

Gly Thr Thr Ala Thr Thr Ala Thr Cys Cys Cys Thr Cys Thr Thr Ala
            20                  25                  30
```

Cys Ala Cys
        35

<210> SEQ ID NO 8
<211> LENGTH: 32
<212> TYPE: PRT
<213> ORGANISM: Clostridium botulinum

<400> SEQUENCE: 8

Cys Thr Cys Gly Ala Gly Thr Ala Ala Gly Thr Ala Cys
1               5                   10                  15

Thr Cys Cys Thr Cys Ala Ala Ala Cys Cys Ala Ala Thr Gly
            20                  25                  30

<210> SEQ ID NO 9
<211> LENGTH: 31
<212> TYPE: PRT
<213> ORGANISM: Clostridium botulinum

<400> SEQUENCE: 9

Gly Gly Ala Thr Cys Cys Gly Ala Ala Gly Thr Thr Gly Ala Thr Ala
1               5                   10                  15

Cys Ala Ala Ala Thr Cys Cys Thr Cys Thr Thr Thr Ala Gly
            20                  25                  30

<210> SEQ ID NO 10
<211> LENGTH: 22
<212> TYPE: PRT
<213> ORGANISM: Clostridium botulinum

<400> SEQUENCE: 10

Gly Gly Ala Thr Cys Cys Gly Ala Thr Ala Thr Cys Ala Gly Cys Cys
1               5                   10                  15

Ala Thr Gly Gly Cys Cys
            20

<210> SEQ ID NO 11
<211> LENGTH: 21
<212> TYPE: PRT
<213> ORGANISM: Clostridium botulinum

<400> SEQUENCE: 11

Thr Ala Ala Cys Thr Cys Gly Ala Gly Cys Ala Cys Cys Ala Cys Cys
1               5                   10                  15

Ala Cys Cys Ala Cys
            20

<210> SEQ ID NO 12
<211> LENGTH: 27
<212> TYPE: PRT
<213> ORGANISM: Clostridium botulinum

<400> SEQUENCE: 12

Thr Thr Cys Thr Gly Gly Thr Gly Gly Thr Gly Gly Ala Thr Thr Thr
1               5                   10                  15

Ala Ala Ala Thr Cys Thr Cys Cys Thr Thr Cys
            20                  25

<210> SEQ ID NO 13
<211> LENGTH: 32
<212> TYPE: PRT
<213> ORGANISM: Clostridium botulinum

```
<400> SEQUENCE: 13

Gly Cys Ala Ala Ala Cys Ala Gly Thr Thr Cys Cys Ala Gly
1               5                   10                  15

Thr Thr Thr Cys Ala Thr Ala Thr Thr Ala Thr Gly Ala Thr Thr Cys
                20                  25                  30

<210> SEQ ID NO 14
<211> LENGTH: 27
<212> TYPE: PRT
<213> ORGANISM: Clostridium botulinum

<400> SEQUENCE: 14

Ala Thr Cys Thr Ala Thr Thr Gly Thr Ala Cys Thr Thr Cys Cys Ala
1               5                   10                  15

Cys Cys Cys Cys Ala Ala Ala Ala Thr Gly Gly
                20                  25

<210> SEQ ID NO 15
<211> LENGTH: 39
<212> TYPE: PRT
<213> ORGANISM: Clostridium botulinum

<400> SEQUENCE: 15

Ala Cys Ala Gly Ala Ala Thr Thr Ala Ala Ala Gly Thr Thr Ala
1               5                   10                  15

Thr Thr Gly Ala Thr Ala Cys Thr Ala Ala Thr Thr Gly Thr Ala Thr
                20                  25                  30

Thr Ala Ala Thr Gly Thr Gly
        35

<210> SEQ ID NO 16
<211> LENGTH: 27
<212> TYPE: PRT
<213> ORGANISM: Clostridium botulinum

<400> SEQUENCE: 16

Ala Thr Thr Ala Gly Thr Ala Thr Cys Ala Ala Thr Ala Ala Cys Thr
1               5                   10                  15

Thr Thr Thr Ala Ala Thr Thr Cys Thr Gly Thr
                20                  25

<210> SEQ ID NO 17
<211> LENGTH: 25
<212> TYPE: PRT
<213> ORGANISM: Clostridium botulinum

<400> SEQUENCE: 17

Cys Thr Thr Ala Ala Thr Cys Thr Ala Gly Thr Ala Ala Thr Ala Ala
1               5                   10                  15

Thr Ala Gly Gly Ala Cys Cys Cys Thr
                20                  25

<210> SEQ ID NO 18
<211> LENGTH: 33
<212> TYPE: PRT
<213> ORGANISM: Clostridium botulinum

<400> SEQUENCE: 18

Ala Cys Cys Ala Cys Cys Thr Ala Thr Cys Ala Cys Ala Thr Thr Ala
1               5                   10                  15
```

```
Ala Thr Ala Cys Ala Ala Thr Thr Ala Gly Thr Ala Thr Cys Ala Ala
            20                  25                  30

Thr
```

<210> SEQ ID NO 19
<211> LENGTH: 21
<212> TYPE: PRT
<213> ORGANISM: Clostridium botulinum

<400> SEQUENCE: 19

```
Gly Gly Thr Gly Gly Thr Ala Gly Thr Thr Ala Thr Ala Gly Ala Thr
1               5                   10                  15

Cys Ala Gly Ala Ala
            20
```

<210> SEQ ID NO 20
<211> LENGTH: 26
<212> TYPE: PRT
<213> ORGANISM: Clostridium botulinum

<400> SEQUENCE: 20

```
Ala Cys Cys Ala Thr Ala Ala Cys Thr Ala Cys Cys Ala Thr Cys Thr
1               5                   10                  15

Gly Gly Thr Thr Gly Thr Ala Thr Cys Ala
            20                  25
```

<210> SEQ ID NO 21
<211> LENGTH: 27
<212> TYPE: PRT
<213> ORGANISM: Clostridium botulinum

<400> SEQUENCE: 21

```
Gly Gly Ala Gly Ala Ala Gly Ala Ala Cys Thr Thr Ala Ala Thr Cys
1               5                   10                  15

Thr Ala Gly Thr Ala Ala Thr Ala Ala Thr Ala
            20                  25
```

<210> SEQ ID NO 22
<211> LENGTH: 26
<212> TYPE: PRT
<213> ORGANISM: Clostridium botulinum

<400> SEQUENCE: 22

```
Thr Cys Thr Ala Gly Ala Ala Cys Thr Gly Gly Ala Thr Gly Gly Thr
1               5                   10                  15

Gly Gly Gly Ala Gly Ala Thr Gly Gly Ala
            20                  25
```

<210> SEQ ID NO 23
<211> LENGTH: 36
<212> TYPE: PRT
<213> ORGANISM: Clostridium botulinum

<400> SEQUENCE: 23

```
Thr Cys Thr Ala Gly Ala Ala Cys Cys Thr Cys Cys Ala Cys Ala Cys
1               5                   10                  15

Ala Cys Ala Gly Gly Ala Ala Cys Cys Ala Gly Thr Gly Gly Ala Thr
            20                  25                  30

Ala Gly Ala Cys
        35
```

<210> SEQ ID NO 24
<211> LENGTH: 37
<212> TYPE: PRT
<213> ORGANISM: Clostridium botulinum

<400> SEQUENCE: 24

Gly Ala Thr Ala Thr Cys Cys Ala Cys Cys Ala Thr Gly Gly Ala Gly
1               5                   10                  15

Thr Cys Ala Cys Ala Gly Ala Cys Thr Cys Ala Gly Thr Cys Thr
                20                  25                  30

Thr Thr Gly Thr Ala
        35

<210> SEQ ID NO 25
<211> LENGTH: 35
<212> TYPE: PRT
<213> ORGANISM: Clostridium botulinum

<400> SEQUENCE: 25

Gly Ala Thr Ala Thr Cys Cys Ala Cys Cys Ala Thr Gly Gly Cys Thr
1               5                   10                  15

Gly Thr Cys Thr Thr Gly Gly Gly Gly Cys Thr Gly Cys Thr Cys Thr
                20                  25                  30

Thr Cys Thr
        35

<210> SEQ ID NO 26
<211> LENGTH: 16
<212> TYPE: PRT
<213> ORGANISM: Clostridium botulinum

<400> SEQUENCE: 26

Gly Thr Ala Ala Ala Ala Cys Gly Ala Cys Gly Gly Cys Cys Ala Gly
1               5                   10                  15

<210> SEQ ID NO 27
<211> LENGTH: 17
<212> TYPE: PRT
<213> ORGANISM: Clostridium botulinum

<400> SEQUENCE: 27

Cys Ala Gly Gly Ala Ala Ala Cys Ala Gly Cys Thr Ala Thr Gly Ala
1               5                   10                  15

Cys

<210> SEQ ID NO 28
<211> LENGTH: 24
<212> TYPE: PRT
<213> ORGANISM: Clostridium botulinum

<400> SEQUENCE: 28

Cys Ala Ala Ala Thr Thr Gly Ala Thr Ala Gly Thr Ala Cys Thr
1               5                   10                  15

Thr Gly Ala Ala Ala Thr Cys Cys
        20

<210> SEQ ID NO 29
<211> LENGTH: 19
<212> TYPE: PRT
<213> ORGANISM: Clostridium botulinum

<400> SEQUENCE: 29

```
Gly Cys Thr Ala Gly Thr Thr Ala Thr Thr Gly Cys Thr Cys Ala Gly
1               5                   10                  15

Ala Gly Gly
```

<210> SEQ ID NO 30
<211> LENGTH: 38
<212> TYPE: PRT
<213> ORGANISM: Clostridium botulinum

<400> SEQUENCE: 30

```
Thr Glu Leu Lys Val Ile Asp Thr Asn Cys Ile Asn Val Ile Gln Pro
1               5                   10                  15

Asp Gly Ser Tyr Arg Ser Glu Glu Leu Asn Leu Val Ile Ile Gly Pro
                20                  25                  30

Ser Ala Asp Ile Ile Gln
        35
```

<210> SEQ ID NO 31
<211> LENGTH: 38
<212> TYPE: PRT
<213> ORGANISM: Clostridium botulinum
<220> FEATURE:
<221> NAME/KEY: misc_feature
<222> LOCATION: (10)..(24)
<223> OTHER INFORMATION: Noncoding Region

<400> SEQUENCE: 31

```
Thr Glu Leu Lys Val Ile Asp Thr Asn Xaa Xaa Xaa Xaa Xaa Xaa Xaa
1               5                   10                  15

Xaa Xaa Xaa Xaa Xaa Xaa Xaa Xaa Leu Asn Leu Val Ile Ile Gly Pro
                20                  25                  30

Ser Ala Asp Ile Ile Gln
        35
```

<210> SEQ ID NO 32
<211> LENGTH: 38
<212> TYPE: PRT
<213> ORGANISM: Clostridium botulinum

<400> SEQUENCE: 32

```
Thr Glu Leu Lys Val Ile Asp Thr Asn Cys Ile Asn Val Ile Gly Gly
1               5                   10                  15

Gly Gly Ser Tyr Arg Ser Glu Glu Leu Asn Leu Val Ile Ile Gly Pro
                20                  25                  30

Ser Ala Asp Ile Ile Gln
        35
```

<210> SEQ ID NO 33
<211> LENGTH: 38
<212> TYPE: PRT
<213> ORGANISM: Clostidium botulinum

<400> SEQUENCE: 33

```
Thr Glu Leu Lys Val Ile Asp Thr Asn Cys Ile Asn Val Ile Gln Pro
1               5                   10                  15

Asp Gly Ser Tyr Gly Gly Glu Glu Leu Asn Leu Val Ile Ile Gly Pro
                20                  25                  30

Ser Ala Asp Ile Ile Gln
        35
```

<210> SEQ ID NO 34

```
<211> LENGTH: 7
<212> TYPE: PRT
<213> ORGANISM: Clostridium botulinum

<400> SEQUENCE: 34

Ser Ser Ala Phe Tyr Pro Lys
1               5

<210> SEQ ID NO 35
<211> LENGTH: 7
<212> TYPE: PRT
<213> ORGANISM: Clostridium Botulinum

<400> SEQUENCE: 35

Thr Arg Gln Pro Asp Arg Ser
1               5

<210> SEQ ID NO 36
<211> LENGTH: 7
<212> TYPE: PRT
<213> ORGANISM: Clostridium Botulinum

<400> SEQUENCE: 36

Thr Leu Gln Pro Asp Arg Ser
1               5

<210> SEQ ID NO 37
<211> LENGTH: 7
<212> TYPE: PRT
<213> ORGANISM: Clostridium Botulinum

<400> SEQUENCE: 37

Ser Leu Gln Pro Asp Arg Ser
1               5

<210> SEQ ID NO 38
<211> LENGTH: 5
<212> TYPE: PRT
<213> ORGANISM: Clostridium Botulinum

<400> SEQUENCE: 38

Gln Pro Asp Arg Ser
1               5

<210> SEQ ID NO 39
<211> LENGTH: 10
<212> TYPE: PRT
<213> ORGANISM: Clostridium Botulinum

<400> SEQUENCE: 39

Gly Val Asp Gly Asp Ile Val Met Thr Gln
1               5                   10

<210> SEQ ID NO 40
<211> LENGTH: 7
<212> TYPE: PRT
<213> ORGANISM: Clostridium Botulinum

<400> SEQUENCE: 40

Thr Leu Val Thr Val Ser Ala
1               5

<210> SEQ ID NO 41
<211> LENGTH: 6
<212> TYPE: PRT
```

```
<213> ORGANISM: Clostridium botulinum

<400> SEQUENCE: 41

Thr Lys Leu Glu Ile Lys
1               5
```

HIGH-AFFINITY MONOCLONAL ANTIBODIES FOR BOTULINUM TOXIN TYPE A

This application claims priority benefit to U.S. provisional application 60/934,530 filed Jun. 13, 2007.

FIELD OF THE INVENTION

The present invention relates to high affinity monoclonal antibodies (Mab's) that bind to heavy and light chains of *Clostridium botulinum* neurotoxin (BoNT) and the associated use of these Mab's in detecting *Clostridium botulinum*.

BACKGROUND OF THE INVENTION

Hybridomas producing *Clostridium botulinum*, an anaerobic spore-forming bacterium, produces a family of botulinum neurotoxins (BoNT, EC 3.4.24.69) [Gill, M. Microbiol. Rev. 46:86-94 (1982)] consisting of seven serotypes, A-G (BoNT/A-BoNT/G). These are considered the most toxic proteins known. Serotype A is synthesized as a single 1,296 amino acid polypeptide, ~150,000 Dalton (Da) that is then cleaved endogenously or exogenously forming a dichain molecule comprised of an ~100 kDa heavy chain (HC) and an ~50 kDa light chain (LC) linked by a single disulfide bond Montecucco, C, and Schiavo, G. Structure and function of tetanus and botulinum neurotoxins. Quarterly Rev. Biophys. 28:423-472 (1995)]. The HC mediates toxin entry into neurons, and the LC functions as a zinc-dependent endoprotease cleaving SNAR proteins involved in acetylcholine release resulting in muscular paralysis [Turton, K., Chaddock, J. A., Acharya, K. R. Trends Biochem. Sci. 27:552-558 (2002)]. The crystal structure of BoNT/A was determined at 3.3 Å resolution [Lacyt, D. B., Tepp, W., Cohen, A. C., DasGupta, B. R., and Stevens, R. C. Crystal structure of botulinum neurotoxin type A and implications for toxicity Nature Structural Biol. 5:898-902 (1998)].

BoNT is synthesized as a single 150 kDa precursor protein, which is cleaved to form two subunit polypeptides, linked by a single disulfide bond. The gold standard for BoNT detection is the mouse bioassay. The mouse bioassay is time consuming, up to 4 days, and lacks specificity, it has a sensitivity in the low pictogram range. Most BoNT immunoassays reported appear to have much less sensitivity than the mouse bioassay.

Bavari et al., U.S. Pat. Nos. 6,667,158 and 7,049,085 have disclosed antibodies to BoNT/A and associated methods of use wherein the affinity of the

SUMMARY OF THE INVENTION

We have characterized four high affinity monoclonal antibodies (Mab). These are IgG1 and IgG2 subclass Mab's with kappa light chains. The Mab specifically bind to BoNT serotype A and have measured Kd values in the low pM range. Western blot analysis demonstrated that three of the Mabs specifically bind the 100 kDa heavy chain subunit, while one of the antibodies specifically binds the 50 kDa light chain. Using a sandwich immunoassay format with a heavy chain specific Mab for capture, a directly labeled anti light chain Mab for detection and a chemiluminescent substrate, detection of BoNT type A in the low picogram range was observed.

Therefore, it is one object of the present invention to provide high affinity monoclonal antibodies (Mab) to *Clostridium botulinum* neurotoxin (BoNT/A).

An object of the present invention is to provide a method for detecting BoNT/A in a sample. The method involves contacting the sample with an antibody which binds an epitope of BoNT/A, allowing the antibody to bind to BoNT/A to form an immunological complex, and detecting the formation of the immunological complex. The increased sensitivity of the assay allows for detection from a variety of sources including biological, environmental and food.

Yet another aspect of the invention is a kit for detecting BoNT/A in a sample. The kit includes a container or platform holding an antibody which binds to an epitope of BoNT/A and instructions for using the antibody for the purpose of binding to BoNT/A form an immunological complex and detecting the formation of the immunological complex such that presence or absence of the immunological complex correlates with presence or absence of BoNT/A.

A further embodiment of the invention is the use of the monoclonal antibodies for treatment of a mammalian organism exposed to *Clostridium botulinum* neurotoxin (BoNT/A) or to serve as a protection agent prior to exposure against the deleterious effects of BoNT/A.

BRIEF DESCRIPTION OF THE DRAWINGS

Figure 14:
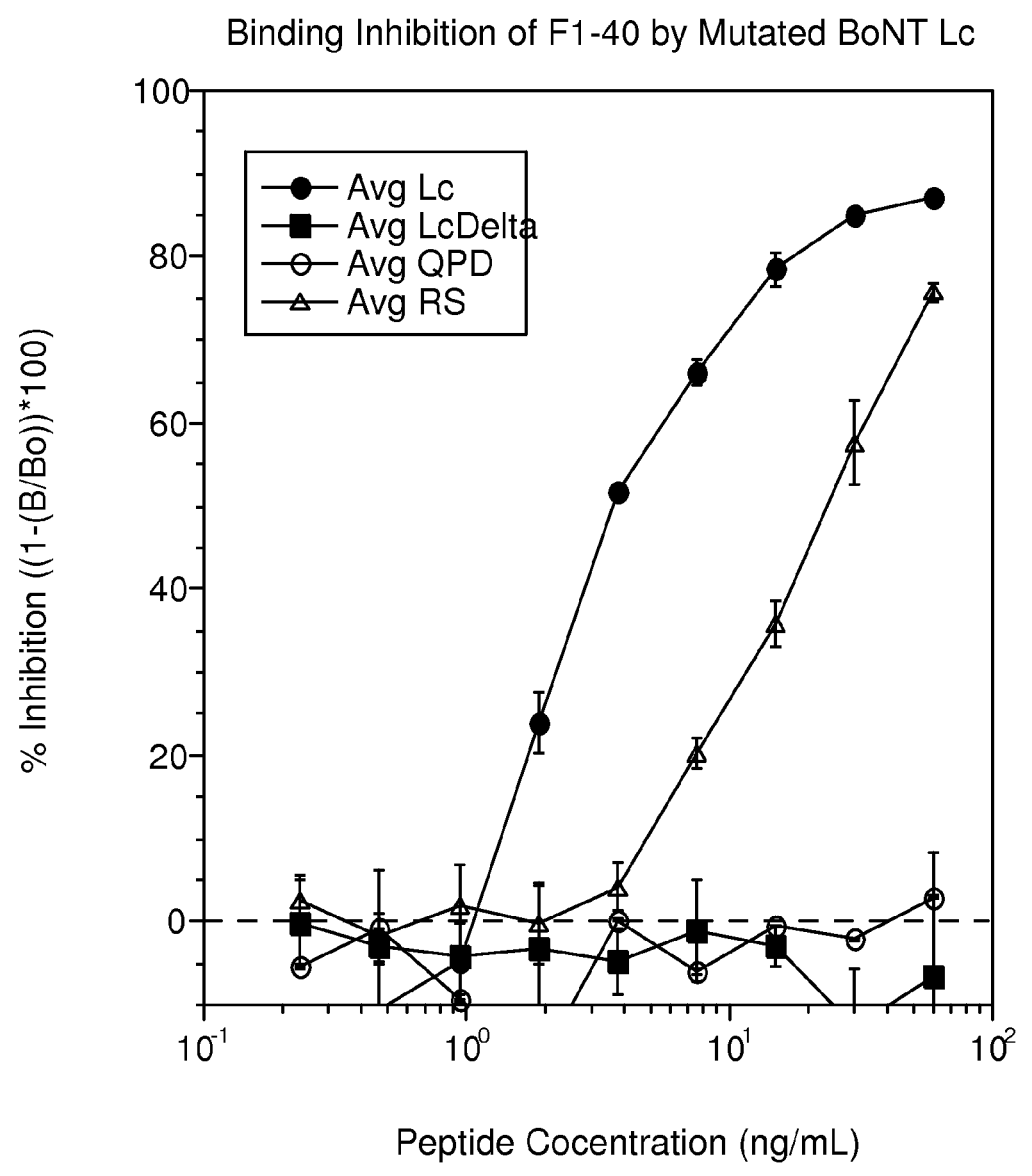

FIG. 14 is a plot of the binding inhibition of F1-40 by Mutated BoNT Lc.

FIG. 19 is a photo of the Western blot of mutations made in the putative F1-40 epitope region on plasmid pGS-Lc and a table of the mutated region (T-125 to Q-162) of the four vectors harboring and expressing the entire BoNT/A light chain. All other amino acids within the light chain were not mutated. Dashes indicate that amino acids have been deleted. Single amino acid mutations are indicated in gray shading.

STATEMENT OF DEPOSIT

Figure 1:
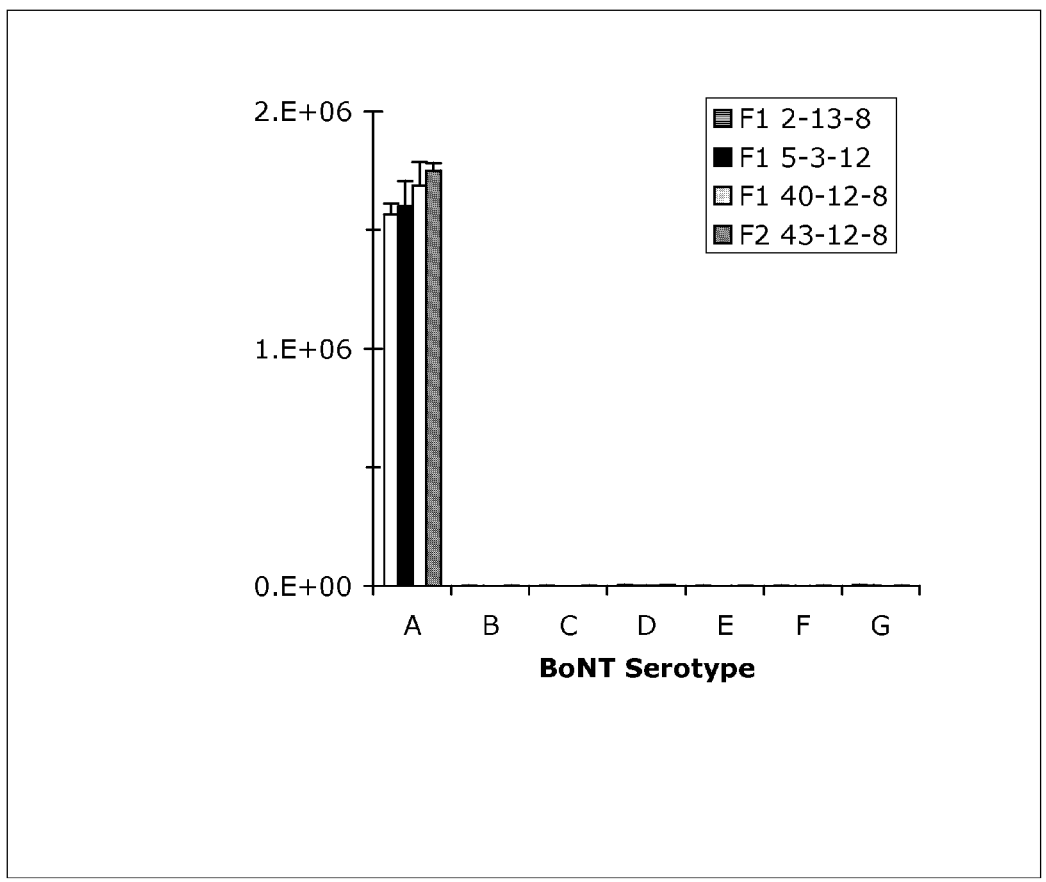
FIG. 1 is a graph of serotype specificity by ELISA. Binding of Mab F1 2-13-8, (horizontal strip) F1 5-3-12 (solid), F1 40-12-8, (stippled) and F2 43-12-8 (diagonal strip) to microtiter wells coated with 0.2 µg/well of the BoNT serotypes A-G. The data shown represents the average of three experiments, error bars represent standard deveation of the mean.

Monoclonal antibodies (Mab) to *Clostridium botulinum* neurotoxin were deposited Apr. 17, 2007 under terms of the Budapest Treaty with the American Tissue Culture Collection (ATCC) P.O. Box 1549, Manassas, Va., 20108, USA. The Mab F1 2-13-8 is produced by the hybridoma deposited under American Type Culture Collection (ATCC) Accession No. PTA-8338 and recognizes BoNT/A and BoNT/Hc. Mab F1 5-3-12 is produced by the hybridoma deposited under American Type Culture Collection (ATCC) Accession No. PTA-8337 and recognizes BbNT/A and BoNT/A Hc. Mab F1 40-12-8 is produced by the hybridoma deposited under American Type Culture Collection (ATCC) Accession No. PTA-8336 recognizes BoNT/A and BoNT/A Lc. The Mab F1 43-12-8 is produced by the hybridoma deposited under American Type Culture Collection (ATCC) Accession No. PTA-8339 and recognizes BoNT/A. The microorganism deposit was made under the provisions of the "Budapest Treaty on the International Recognition of the Deposit of Microorganisms for the Purposes of Patent Procedure". All restrictions on the availability to the public of these deposited microorganisms will be irrevocably removed upon issuance of a United States patent based on this application. For the purposes of this invention, any Mab having the identifying characteristics of PTA-8336, PTA-8337, PTA-8338 or PTA-8339, including subcultures and variants thereof which have the identifying characteristics and activity as described herein are included.

DESCRIPTION OF THE INVENTION

The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement.

*Clostridium botulinum*, an anaerobic spore-forming bacterium, produces a family of botulinum neurotoxins (BoNT, EC 3.4.24.69) [Gill, M. Microbiol. Rev. 46:86-94 (1982)] consisting of seven serotypes, A-G (BoNT/A-BoNT/G). These are considered the most toxic proteins known. Serotype A is synthesized as a single 1,296 amino acid polypeptide, 150,000~Daltons (Da) that is then cleaved endogenously or exogenously forming a dichain molecule comprised of an ~100 kDa heavy chain (HC) and an ~50 kDa light chain (LC) linked by a single disulfide bond [Montecucco, C, and Schiavo, G. Structure and function of tetanus and botulinum neurotoxins. Quarterly Rev. Biophys. 28:423-472 (1995)]. The HC mediates toxin entry into neurons, and the LC functions as a zinc-dependent endoprotease cleaving SNAR proteins involved in acetylcholine release resulting in muscular paralysis [Turton, K., Chaddock, J. A., Acharya, K. R. Trends Biochem. Sci. 27:552-558 (2002)]. The crystal structure of BoNT/A was determined at 3.3 Å resolution [Lacyt, D. B., Tepp, W., Cohen, A. C., DasGupta, B. R., and Stevens, R. C. Crystal structure of botulinum neurotoxin type A and implications for toxicity Nature Structural Biol. 5:898-902 (1998)].

An embodiment of the invention describes high affinity monoclonal antibodies (Mab's) to heavy and light chains of *Clostridium botulinum* neurotoxin A. The antibodies are $IgG_1$ subclass Mab's with kappa light chains that specifically bind BoNT serotype A (BoNT/A). Specifically, Mab's binding to the 150 kDa toxin, the 100 kDa heavy-chain subunit and the Mab binding to the 50 kDa light-chain. Further characterization of these Mab's and their application to rapid immunoassay formats is presented.

A further embodiment of the invention describes the use of the Mab's in a test kit for the detection of *Clostridium botulinum*. In this application a HC specific Mab is immobilized on the surface of a microtiter well and functions as a capture antibody. Toxin contaminated samples are then added to the microtiter well and the toxin allowed to bind the immobilized HC Mab. This step acts to both capture and concentrate the toxin from the sample. Next the well is washed with buffer to remove nonreacted materials. This step removes nonreacted test material thereby removing any compounds in the test sample that might interfer with the assay. The toxin bound to the immobilized antibody remains. Next, the bound toxin is detected by addition of a second anti-toxin antibody, in this example the LC specific Mab that has had biotin chemically coupled to itself. Again non reacted materials are removed by washing and an Avidin-horseraddish Peroxidase reagent is added. Following a final washing step toxin is then detected by adding an appropriate substrate, in this example a substrate is added that when cleaved by the horseradish Peroxidase results in a luminescent signal that can be recorded in a spectrophotometer. Enzymes other that horseradish Peroxidase can be used, i.e., alkaline phosphatase or urease, and other substrates, luminescent, fluorescent, or chromogenic, designed for the specific enzyme used can be used to detect the presence of bound toxin. Using the above test, toxin can be detected in amounts less than that detected by the mouse bioassay.

The term "antibody" (Ab) or "monoclonal antibody" (Mab) as used herein is meant to include intact molecules as well as fragments thereof (such as, for example, Fab and F(ab').sub.2 fragments) which are capable of binding. The language "monoclonal antibody" is art-recognized terminology. The monoclonal antibodies of the present invention can be prepared using classical cloning and cell fusion techniques. The immunogen (antigen) of interest, e.g. intact 150 kDa toxin, or separated heavy or light chains of BoNT/A, is typically administered (e.g. intraperitoneal injection to wild-type mice or transgenic mice which produce desired antibodies, such as human antibodies, rats, rabbits or other animal species which can produce native or human antibodies. The immunogen can be administered alone or as a fusion protein to induce an immune response. Fusion proteins comprise the peptide against which an immune response is desired coupled to a carrier protein, such as .beta.-galactosidase, glutathione S-transferase, keyhole limpet hemocyanin (KLH), and bovine serum albumin, to name a few. In these cases, the peptides serve as haptens with the carrier proteins. After the animal is boosted, for example, three or four times, the spleen is removed and splenocytes are extracted and fused with myeloma cells using the well-known processes of Kohler and Milstein (Nature 256: 495-497 (1975)) and Harlow and Lane (Antibodies: A Laboratory Manual (Cold Spring Harbor Laboratory, New York 1988)). The resulting hybrid cells are then cloned in the conventional manner, e.g. using limiting dilution, screened and the resulting positive clones, which produce the desired monoclonal antibodies, cultured.

The term "epitope" is art-recognized. It is generally understood by those of skill in the art to refer to the region of an antigen, such as BoNT/A, that interacts with an antibody. An epitope of a peptide or protein antigen can be formed by contiguous or noncontinguous amino acid sequences of the antigen.

Antibodies, or fragments thereof, may be labeled using any of a variety of labels and methods of labeling. Examples of types of labels which can be used in the present invention include, but are not limited to, enzyme labels, radioisotopic labels, non-radioactive isotopic labels, chromogenic labels, fluorescent labels, and chemiluminescent labels [Harlow and Lane, Antibodies: A Laboratory Manual (Cold Spring Harbor Laboratory, New York 1988) 555-612].

The present invention still further pertains to a method for detecting BoNT/A in a sample containing BoNT/A. The method includes contacting the sample with an antibody which binds an epitope of BoNT/A, allowing the antibody to bind to BoNT/A to form an immunological complex, and detecting the formation of the immunological complex and correlating presence or absence of the immunological complex with presence or absence of BoNT/A in the sample. The sample can be biological, environmental or a food sample.

A further embodiment of the invention is the use of the monoclonal antibodies for in vivo treatment of exposure or infection to *Clostridium botulinum* neurotoxin (BoNT/A) or to serve as a vaccine or therapeutic agent wherein protection may be afforded via administration of the antibodies to those at risk of exposure or wherein infection or presence of the toxin within the organism has been detected.

The antibodies of the invention have a binding affinity of about $8.0 \times 10^{-12}$ Kd. The term neutralizing as herein refers to an antibody that specifically binds to a BoNT/A poplypeptide, wherein the binding reduces the toxicity of the BoNT/A polypeptide. The neutralization capacity of the antibodies is also an embodiment of vaccines or therapeutic agents and adjuvants described herein. Reduced toxicity can be measured as an increase in the time that paralysis developed and/or as a lethal dosage (e.g. $LD_{50}$) as described herein. Antibodies derived from BoNT/A neutralizing antibodies include the antibodies whose sequence is provided herein. It will be appreciated that mimotypes of the said antibodies can be used in accordance with the present invention. The term mimotype, as used herein, means a peptide, or peptide derivative, specifically synthesized to bind the paratope of a given antibody.

The language "detecting the formation of the immunological complex" is intended to include discovery of the presence or absence of BoNT/A in a sample. The presence or absence of BoNT/A can be detected using an immunoassay. A number of immunoassays used to detect and/or quantitate antigens are well known to those of ordinary skill in the art. See Harlow and Lane, Antibodies: A Laboratory Manual (Cold Spring Harbor Laboratory, New York 1988. These assays are commonly used by those of ordinary skill in the art. In an antibody capture assay, the antigen is attached to a solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a BoNT/A vaccinee, and a monoclonal antibody of the present invention, are allowed to compete for binding of the antigen. The amount of monoclonal bound is then measured, and a determination is made whether the serum contains anti BoNT/A antibodies wherein detection of large amounts of monoclonal antibody indicates a small to no antibody against BoNT/A in the serum. This competitive ELISA can be used to predict immunity in a vaccinee following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen. These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), Schurs, A. H. W. M., et al. 1977 (Clin. Chim Acta 81:1-40), Bobrovnik, S. A. 2003 (J. Biochem. Biochys. Methods 57:213-236), and Friguet et al 1985 (J. Immunol. Methods 77:305-319).

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, betagalactosidase, ribonuclease, urease, catalase, glucose-6-phosphate dehydrogenase, glucoamylase, acetylcholine esterase, etc.

Examples of suitable radioisotopic labels include $^3H$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, and $^{109}Pd$.

Examples of suitable fluorescent labels include an $^{152}Eu$ label, a fluorescein label, an isothiocyanate label, a rhodamine label, a phycoerythrin label, a phycocyanin label, an allophycocyanin label, an o-phthaldehyde label, a fluorescamine label, etc.

Examples of chemiluminescent substrates include a luminal substrate, an isoluminal substrate, an aromatic acridinium ester substrate, an imidazole substrate, an acridinium salt substrate, an oxalate ester label, a luciferin substrate, a luciferase label, an aequorin label, etc.

TABLE 1

Comparison of Luminescent Immunoassay to ELISA using a colorimetric substrate. Antisera from immunized mice used in cell fusion experiments.

| Antisera Dilution Factor | Luminescent (Counts) | Signal: Noise | Colorimetric (Absorbency) | Signal: Noise |
|---|---|---|---|---|
| 500 | 5,557,000 | 3,175 | 1.60 | 22.6 |
| 1,000 | 5,078,000 | 2,9017 | 1.40 | 23.3 |
| 10,000 | 2,228,934 | 1274 | 0.21 | 35 |
| 100,000 | 477,000 | 273 | 0.09 | 1.5 |
| 500,000 | 98,000 | 56 | 0.08 | 1.3 |
| 1,000,000 | 55,352 | 32 | 0.07 | 1.2 |
| 2,000,000 | 28,426 | 16 | 0.07 | 1.2 |
| Blank | 1,750 | | 0.06 | |

Examples of monoclonal antibodies raised against BoNT/A using this method include MAb ATCC accession numbers thymidine (8 µM) to complete hybridoma medium. Macrophage conditioned media (MΦDCM) was prepared as described (Sugasawara et al. 1985).

Female Balb/cJ mice (Simonsen Laboratories, Gilroy, Calif.) were housed in the institutional small animal facility under AAALAC standards and all protocols were approval by the institutional animal care and use committee. Mice were immunized (2-week intervals) by intraperitoneal injection (IP) of 100 µL of BoNT serotype A toxoid (List Laboratories, Cat # 133) prepared in RIBI adjuvant as suggested by the manufacturer. Following the third injection, serum was obtained and evaluated for anti-BoNT antibodies. Mice with a strong antibody titer were rested for two weeks and given an IP injection with 1 µg of toxoid in PBS.

Three days following the last IP injection, splenocytes were fused with SP2/0 myeloma cells using polyethylene glycol as previously described (Bigbee et al., 1983). Following cell fusion, the cells were suspended in 100 mL of HAT selection medium supplemented with 10% fetal calf serum and 10% macrophage conditioned media, dispensed into 10, 96-well tissue culture plates, and incubated 10 to 14 days at 37° C. in 5% $CO_2$ before to screening for antibody production.

Example 2

Screening/ELISA Methods

Sera from immunized mice and supernatants from the cell fusion plates were screened using a direct binding ELISA. Microtiter plates (Nunc MaxiSorp Black) were rinsed with reverse osmosis (R.O.) water and then were coated with BoNT by incubating 100 µL/well of a 0.2 µg/mL solution of BoNT/A in 0.05M Carbonate Buffer, pH 9.6 overnight at 4° C. The toxin was aspirated and non reacted sites blocked by adding 400 µL/well of a 5% NFDM-TBS-0.05% TWEEN® 20 (TBS-T) solution and the plates were incubated for 1 hr at 37° C. The plate was then washed 3 times with 0.05% tween-water. Next sera or cell culture supernatant was added (100 µL/well) and the plate incubated at 37° C. for 1 hr. Plates were again washed (3×) and 100 µL/well of a 1/5000 dilution of peroxidase-conjugated goat anti-mouse sera (Sigma, St. Louis, Mo.) was added and the plates incubated for 1 hr at 37° C. The plates were then washed 6× with 0.05% solution of Tween-20 prepared in R.O.water. Freshly prepared (according to manufacturers recommendation) Super signal luminescent Femto Max Sensitivity (Pierce Inc. Cat #37074 Rockford, Ill.) substrate was added. The plates were incubated for 3 min at room temperature and luminescent counts recorded using a Perkin-Elmer Model Victor$^2$ microplate reader.

Cells from wells giving positive signals were cloned by limited dilution. Cells from antibody-producing wells were then expanded in cell culture and small amounts (usually less than 10 mLs) of ascites fluids obtained. Resulting hybridoma cell-lines were maintained in Iscove's modified Dulbecco's minimal medium, Sigma (#1-7633), containing $NaHCO_3$ (36 mM), glutamine (2 mM), and fetal calf serum (5%) (cHM) and used for production of antibody by inducing an ascites tumor. Ascites fluids were prepared by Covance Research Products Inc. (Denver, Pa.) and were purified by affinity chromatography on Protein-G Sepharose. Bound antibody was eluted with 0.1M Glycine-HCl pH 2.7. Protein concentrations were determined with a BCA-kit (Pierce, Rockvill, Ill.) using the microtiterplate method suggested by the manufacturer. Antibodies were conjugated with biotin using EZ-Link Sulfo-NHS-LC-Biotin (Pierce, Rockford, Ill.) as described by the manufacturer using a 50-fold molar excess of biotin reagent. Antibody isotype was determined by ELISA using toxin-coated microtiter plates and horseradish Peroxidase-conjugated, isotype-specific antibodies (Southern Biotechnologies. Sigma, Saint Louis, Mo.).

Example 3

Isolation of Serotypes/Binding Affinity of Mab's

Toxins were separated using 4-20% polyacrylamide gels (PAGEgel Inc., San Diego, Calif.) as recommended by the manufacturer. Samples were suspended in electrophoresis sample buffer and 10 µL containing 100 ng of protein were loaded into each well and separated by electrophoresis at 200 V (constant). Following electrophoresis proteins were electrophretically transferred to PVDF membranes using a PAGEgel transfer cell as recommended by the manufactured (180 mA constant for 90-120 min). Filters were blocked with 3% NFDM-PBS-0.05% tween buffer (PBST) for 1 hr at 22° C. on a rocking platform The membranes were then washed 3× for 5 min each (with rocking) in PBST, primary anti-toxin antibody was added (1 µg/mL) and the membranes incubated overnight at 4° C. The membranes were again washed 3× for 5 min each, Peroxidase conjugated goat anti-mouse IgG (whole molecule) antiserum (Sigma, St. Louis, Mo. #A4416) diluted 1:50,000 in PBST and incubated with rocking at 22° C. for 1 hr. The membranes were then washed 3×, 5 min each, and Super Signal (Pierce, Rockford, Ill., #34075) substrate added as recommended by the manufacturer. Filters were placed between plastic sheets (page protectors) and bands visualized using Kodak BioMax XAR film (Eastman Kodak Co, Rochester, N.Y.) or using a FluoroChem Sp gel imaging system (Alpha Innotech Inc. San Leandro. CA). Direct visualization of proteins following SDA-PAGE used silver staining (Silver Express, Invitrogen Inc., Grand Island, N.Y.) as described by the manufacturer.

The binding dissociation constant ($K_D$) was measured by ELISA using the method described by Friguet, et al., (1985). Data analysis and calculation of the $K_D$ used the improved methods described by Bobrovnik (2003) the following relationship.

$$Ao-Ai/Ai=Kali \qquad (1)$$

Where Ao equals the activity measured when no toxin was present; Ai, the activity measured when different amounts of toxin ($833-4.2\times10^{-12}$ Molar toxin) was added, and li equals the variable concentration of toxin 833- to $4.2\times10^{-12}$ Molar). The value of Ka was determined graphically as the slope of the linear relation depicted in equation 1. Kd was determined from the relation $$Ka=1/Kd.$$

Antibody concentration in these experiments was 40 pMolar.

Figure 2:
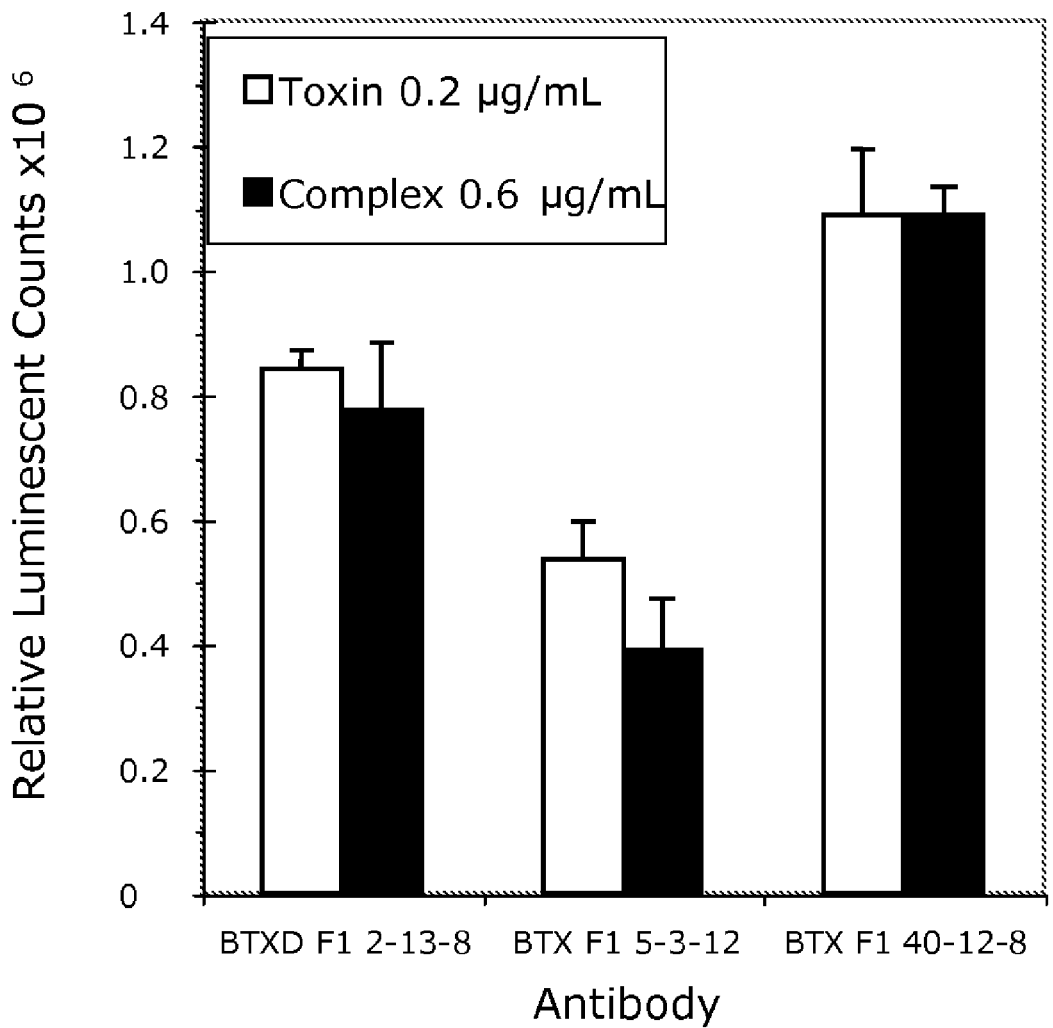
FIG. 2 shows the binding of antibodies F1 2-13-8, F1 5-3-12, F1 40-12-8 to purified BoNT/A toxin (open bar) and BoNT/A complex (solid bar) in an ELISA. Microtiter wells were coated with toxin at 0.2 µg/mL and with BoNT/A complex at 0.6 µg/mL.
Figure 3:
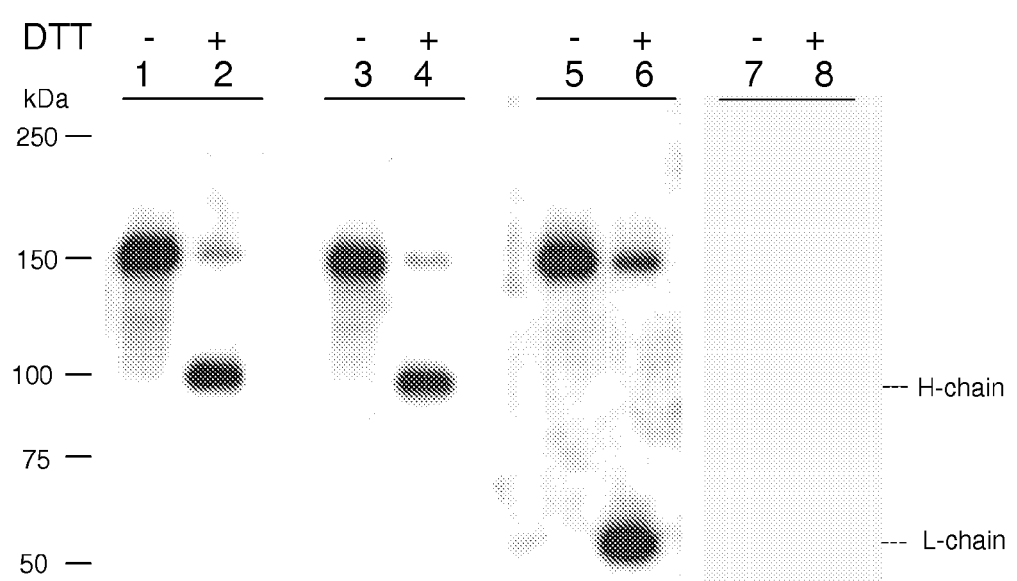
FIG. 3 is a graph of a Western blot of BoNT/A with and without reduction of the disulfide bond. BoNT/A was separated on 4-20% SDS-PAGE in the presence and absence of 1 mM DTT, transferred to membranes and probed with Mabs F1 2-13-8 (lanes 1-2) F1 5-3-12 (lanes 3-4), F1 40-12-8 (lanes 5-6) and F2 43-12-8 (lanes 7-8).

Seven distinct serotypes of BoNT (A-G) are known. The binding profile of each of the 4 anti-BoNT Mab's (F1 2-13-8, F1 5-3-12, F1 40-12-8, and F2 43-12-8), to the seven toxin serotypes was determined by ELISA. Results from these experiments (see FIG. 1) demonstrate that all of the Mab's strongly bind BoNT seroytype A with virtually no binding to the other six BoNT serotypes (types B-G). Since the BoNT is a dichain molecule linked by a single disulfide bridge, western blots of reduced and nonreduced toxin were probed with each Mab to determine if the antibodies specifically bound the heavy- or light-chain. In these experiments, Mab's F1 2-13-8, F1 5-3-12, and F1 40-12-8 labeled the 150 kDa toxin in the nonreduced samples (FIG. 2). In addition, F1 2-13-8, and F1 5-3-12 specifically labeled the heavy-chain of BoNT when the samples were reduced (FIG. 2, lanes 2 and 4) as well as a small amount of nonreduced 150 kDa toxin but no labeling of the BoNT light-chain was observed. In contrast, Mab F1 40-12-8 labeled the light-chain but not the heavy-chain of BoNT in reduced samples (lane 6). Unlike the above Mab's, F2 43-12-8 did not label the intact BoNT or the separated neurotoxin chains on western blots (FIG. 2, lanes 5-6). However, F2 43-12-8 did demonstrate strong activity in the ELISA (FIG. 1). Comparable antibody binding also was observed in direct binding ELISA experiments when the 900 kDa BoNT Complex was used as antigen (FIG. 3).

Figure 4:
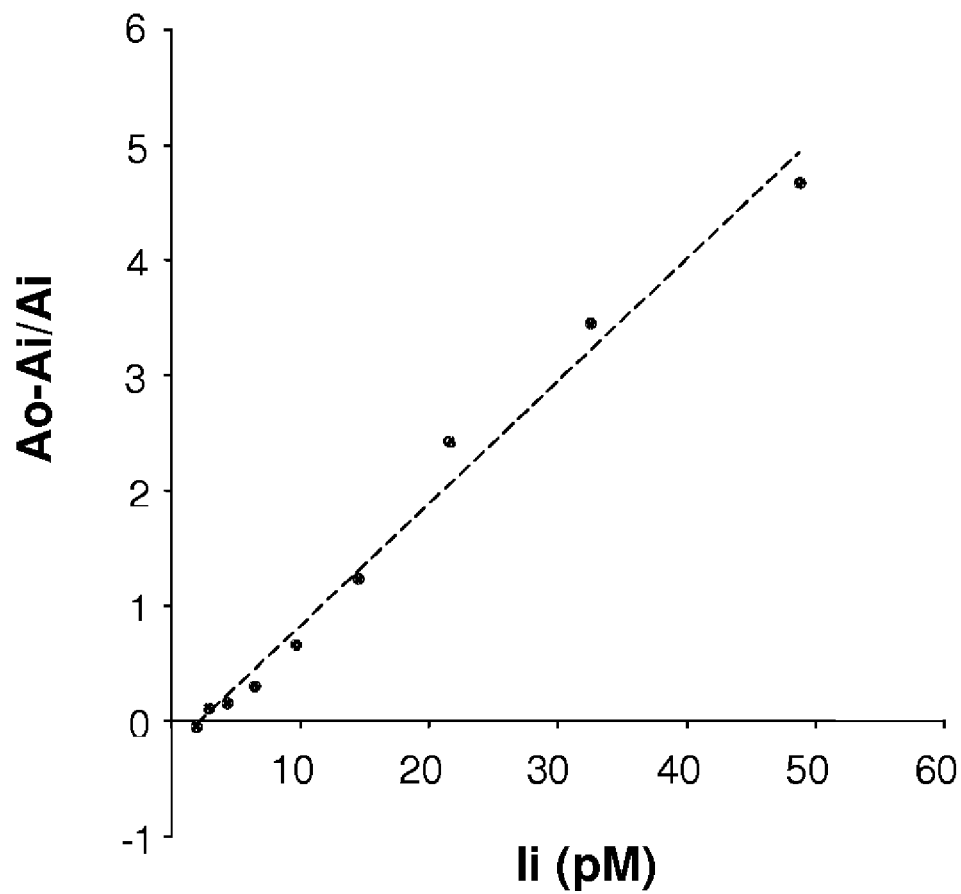
FIG. 4 is a Scatchard plot of the binding of BoNT/A holotoxin to Mab F1 2-13-8 measured by ELISA using equation 6 [Ao−Ai/Ai=Kali,] of Bobrovnik (2003).

The capture dissociation constant was determined for each antibody using both purified 150 kDa BoNT/A and 900 kDa toxin complex and these data are summarized in Table 2. Typical data, for Mab F1 2-13-8 is shown in FIG. 4 where the Kd value was deduced from the inverse of the slope calculated from linear regression analysis. These data demonstrate that the monoclonal antibodies described here have capture dissociation constants in the low pM range for both the 150 kDa holotoxin and the 900 kDa complex.

Example 4

Neutralization Assay

The capability of the Mabs to neutralize BoNT/A was determined using a mouse bioassay in which toxin and varying concentrations of antibody are premixed and then injected. In these experiments the time to death and number of surviving mice was determined. Compared with toxin alone, three of the monoclonal antibodies, F1 2-13-8, F1 5-3-12 and F1 40-12-8, when used at the higher antibody concentrations, significantly increased the time to neuroparalysis and death. Thus, these monoclonal antibodies are individually capable of neutralizing the intact 150 kDa toxin. In contrast, monoclonal antibody F2 43-12-8 was not observed to neutralize the intact 150 kDa toxin. The similar results were observed for the 900 kDa BoNT/A complex. Antibodies F1 2-13-8, F1 5-3-12, and F1 40-12-8 were able to neutralize the complex where as antibody F2 43-12-8 did not neutralize the complex (see Figures).

Epitope Characterization

Identification of the F1-40 epitope on the light chain of BoNT/A using three complementary experimental approaches. Firstly, antibody binding to recombinant peptide fragments of BoNT/A light-chain was used in Western blots to identify the epitope regions. Secondly, a peptide phage-display library was used to identify specific amino acid ligands to F1-40. Thirdly, the three-dimensional structure of BoNT/A was examined in silico, and the ligands determined from the phage-display studies were mapped onto the three-dimensional structure in order to visualize the epitope. Mutagenesis studies were then used to confirm the identified epitope. The variable regions of the heavy and light chains of antibody F1-40 were cloned from mRNA extracts, and the sequences of the complementarity determining regions were deduced.

a. Plasmid Construction

Commercial enzymes (Phusion High-Fidelity DNA Polymerase, BamHI, XhoI, T4 polynucleotide kinase [3' phosphatase minus], T4 DNA ligase [New England BioLabs Inc., Bethesda, Md.]) were used according to the manufacturer's recommendation. Primers used were purchased from Integrated DNA Technologies (Coralville, Iowa) and are shown in Table 1. Plasmid construction and manipulation was performed in *Escherichia coli* TOP10 cells (Invitrogen, Carlsbad, Calif.) grown aerobically in Luria-Bertani (LB) medium at 37° C. supplemented with 100 µg/mL ampicillin (Miller, 1972). Plasmids or DNA were purified using the QuickClean 5M range of kits (GenScript Corp., Piscataway, N.J.). All automated DNA sequencing was performed using the Big Dye Terminator Version 3.1 and XTerminator reagents, and a 3730 DNA Analyzer (Applied Biosystems, Foster City, Calif.)

Total genomic DNA from *Clostridium botulinum* (Strain ATCC3502) was used as a template to amplify the fragments of the light chain (Lc, L1, L2) using the primers indicated (see Table 2). Stop codons (TAA) were introduced when not present within the genomic DNA of the cloned region. All subsequent BoNT/A DNA fragments were cloned into plasmid pCR4-TOPO (Invitrogen) to allow sequencing using primers M13F and M13R. The pCR4-derived plasmids were then digested using BamHI and XhoI, the BoNT/A fragment was purified and ligated into BamHI- and XhoI-digested pGS-21a (Genscript) to yield the correspondently named pGS plasmid (e.g. pGS-L1 for fragment L1). All pGS-21a-derived plasmids were sequenced using primer pGS-F and pGS-R, to confirm the correct integration of the BoNT/A fragment into the vector. The BamHI and XhoI cloning sites of pGS-21a are located downstream of glutathione-S-transferase (GST), under the control of the T7 promoter.

Plasmids pGS-L1-1 through pGS-L1-4 were constructed by PCR using plasmid pGS-L1 as a template. Primers were used to amplify outwards from the L1 region, thus eliminating internal pieces of L1. The PCR product was gel purified, treated with T4 polynucleotide kinase then self-ligated to form an intact plasmid. Plasmids pGS-Lc-Δ, pGS-Lc-QPD and pGS-Lc-RS were constructed by PCR in an identical manner, using plasmid pGS-Lc as a template, and the primers shown in Table 2.

TABLE 2

Primers. Sites for restriction enzymes BamHI (GGATCC), XhoI (CTCGAG), XbaI (TCTAGA) and EcoRV (GATATC) are shown underlined. Stop codons are shown in bold. The third column indicates which peptide fragments each primer was used to construct, or where the primer was used to clone the heavy and light chain variable regions of F1-40. Primers used only for sequencing are indicated by the abbreviation "seq."

| Primer | Sequence | Constructs | SEQ ID NO: |
|---|---|---|---|
| LcF | GGATCCATGCCATTTGTTAATAAACAATTTAATTATAAAG | Lc, L1 | SEQ ID NO:6 |
| LcR | CTCGAGTTATTTAGAAGTTATTATCCCTCTTACAC | Lc, L2 | SEQ ID NO:7 |

TABLE 2-continued

Primers. Sites for restriction enzymes BamHI (GGATCC), XhoI (CTCGAG), XbaI (TCTAGA) and EcoRV (GATATC) are shown underlined. Stop codons are shown in bold. The third column indicates which peptide fragments each primer was used to construct, or where the primer was used to clone the heavy and light chain variable regions of F1-40. Primers used only for sequencing are indicated by the abbreviation "seq."

| Primer | Sequence | Constructs | SEQ ID NO: |
|---|---|---|---|
| L1R | CTCGAGTTAAAGTGACTCCTCAAAACCAAATG | L1 | SEQ ID NO:8 |
| L2F | GGATCCGAAGTTGATACAAATCCTCTTTTAG | L2 | SEQ ID NO:9 |
| GS-L | GGATCCGATATCAGCCATGGCC | L1-3, L1-4 | SEQ ID NO:10 |
| GS-R | TAACTCGAGCACCACCACCAC | L1-1, L1-2 | SEQ ID NO:11 |
| L1b | TTCTGGTGGTGGATTTAAATCTCCTTC | L1-1 | SEQ ID NO:12 |
| L1c | GCAAAACAAGTTCCAGTTTCATATTATGATTC | L1-4 | SEQ ID NO:13 |
| L1d | ATCTATTGTACTTCCACCCCAAAATGG | L1-2 | SEQ ID NO:14 |
| L1e | ACAGAATTAAAAGTTATTGATACTAATTGTATTAATGTG | L1-3 | SEQ ID NO:15 |
| Lc-ΔL | ATTAGTATCAATAACTTTTAATTCTGT | Lc-Δ | SEQ ID NO:16 |
| Lc-ΔR | CTTAATCTAGTAATAATAGGACCCT | Lc-Δ | SEQ ID NO:17 |
| Lc-QPDL | ACCACCTATCACATTAATACAATTAGTATCAAT | Lc-QPD | SEQ ID NO:18 |
| Lc-QPDR | GGTGGTAGTTATAGATCAGAA | Lc-QPD | SEQ ID NO:19 |
| Lc-RSL | ACCATAACTACCATCTGGTTGTATCA | Lc-RS | SEQ ID NO:20 |
| Lc-RSR | GGAGAAGAACTTAATCTAGTAATAATA | Lc-RS | SEQ ID NO:21 |
| L-chainR | TCTAGAACTGGATGGTGGGAGATGGA | F1-40 L-chain cloning | SEQ ID NO:22 |
| H-chainR | TCTAGAACCTCCACACACAGGAACCAGTGGATAGAC | F1-40 H-chain cloning | SEQ ID NO:23 |
| L-chainF3 | GATATCCACCATGGAGTCACAGACTCAGGTCTTTGTA | F1-40 L-chain cloning | SEQ ID NO:24 |
| H-chainF3 | GATATCCACCATGGCTGTCTTGGGCTGCTCTTCT | F1-40 H-chain cloning | SEQ ID NO:25 |
| M13F | GTAAAACGACGGCCAG | seq. pCR4 plasmids | SEQ ID NO:26 |
| M13R | CAGGAAACAGCTATGAC | seq. pCR4 plasmids | SEQ ID NO:27 |
| pGS-F | CAAATTGATAAGTACTTGAAATCC | seq. pGS-21a plasmids | SEQ ID NO:28 |
| pGS-R | GCTAGTTATTGCTCAGAGG | seq. pGS-21a plasmids | SEQ ID NO:29 | b. Expression and Purification of GST-Fusion Proteins

All pGS-21a-derived plasmids were transformed into *E. coli* BL21-CodonPlus (DE3)-RIPL cells (Stratagene, La Jolla, Calif.), and grown aerobically on LB agar at 37° C. supplemented with 100 μg/mL ampicillin and 75 μg/mL streptomycin. Single colonies were grown overnight in LB containing the same antibiotics and 0.5% glucose, to minimize uninduced expression of the fusion protein (Hengen, 1996). An inoculum of 6 mL was added to 600 mL 2YT medium (1% tryptone, 1.6% yeast extract, 0.5% NaCl) containing the same antibiotics and glucose, and the culture was grown aerobically at 30° C. with 200 rpm agitation to an $OD_{600}$ of ~0.6. Expression was induced with 1 mM IPTG, the culture was grown overnight at 18° C. and cells were harvested by centrifugation at 10000×g for 10 min.

The cell pellet was suspended in 10 mL lysis solution (PBS [10 mM phosphate buffer, 138 mM NaCl, 2.7 mM KCl, pH 7.4], 1 mM PMSF, 0.2 mg/mL lysozyme, 1× CelLytic-B Cell Lysis Reagent, 0.5 μL Benzonase Nuclease [Sigma-Aldrich Inc., St. Louis, Mo.]) and incubated at 37° C. for 10 min with 200 rpm agitation, then placed immediately on ice. The lysate was clarified by centrifugation at 12800×g for 15 min, then loaded directly onto a column of High-Affinity GST Resin (1 mL bed volume; Genscript) that had been equilibrate with 20 bed volumes ice-cold PBS containing 1 mM PMSF. The column was washed with 30 bed volumes ice-cold PBS-PMSF and then eluted with 15 bed volumes of elution buffer (10 mM reduced glutathione, 50 mM Tris, pH 8.0) in fractions of 1 mL.

c. Electrophoresis and Western Blots

All gel electrophoresis equipment, buffers, gels and nitrocellulose membranes were purchased from PAGEgel (San Diego, Calif.). Samples of 40 μL (25 μL protein sample, 10 μL 4× gel buffer, 4 μL 1M dithiothreitol) were heated for 10 min at 70° C., then loaded onto a 10% gel and separated by electrophoresis at 175 V (constant) for 80 min. For protein visualization, gels were silver stained using the Silver Express kit (Invitrogen) according to manufacturer's instructions. For Western blotting, the gel was subjected to horizontal blotting onto a nitrocellulose membrane using a PAGEgel transfer cell (180 mA constant, 100 min). Membranes were incubated in blocking buffer (1×PBS-T [PBS plus 0.05% Tween], 3% non-fat dried milk) for 1 hr at room temperature with gentle agitation. Membranes were incubated for 1 hr at 37° C. with gentle agitation in primary antibody (F1-40 or a rabbit polyclonal to *Clostridium botulinum* A toxoid #20641 [Abcam Inc., Cambridge, Mass.]) diluted 5 μg/mL in 10 mL of blocking buffer. Membranes were washed 4 times in PBS-T. Membranes were incubated for 1 hr at room temperature with gentle agitation in secondary antibody diluted 1:5000 in blocking buffer. Peroxidase-conjugated, goat anti-mouse IgG #A4416 was used to detect F1-40; peroxidase-conjugated, goat anti-rabbit IgG #A6154 was used to detect the polyclonal antibody (Sigma-Aldrich). Membranes were washed 4 times in PBS-T, then SuperSignal West Dura Extended Duration Substrate (Pierce, Rockford, Ill.) was added according to manufacturer's instructions. Membranes were visualized using a Fluorchem SP unit (Alpha Innotech Corp., San Leandro, Calif.).

d. Competition ELISA

Black 96-well plates were coated with the Lc-GST fusion peptide by adding 100 μL per well of a 4 μg/mL solution of Lc peptide in 0.5 M carbonate buffer (pH 9.6) and incubating overnight at 4° C. Plates were then blocked by adding 300 μL blocking buffer (1×PBS-T [PBS plus 0.05% Tween], 3% non-fat dried milk) to each well and incubating for 1 hr at room temperature. Wells were filled with 100 μL blocking buffer containing decreasing concentrations (120, 60, 30, 15, 7.5, 3.75, 1.88, 0.94, and 0 μg/mL) of a fusion peptide in solution (Lc, Lc-Δ, Lc-QPD or Lc-RS) and then 100 μL of a 5 μg/mL solution of F1-40 was immediately added to each well. Plates were incubated overnight at 4° C. with gentle agitation, then washed 12 times in PBS-T. Next, 200 μL of peroxidase-conjugated goat anti-mouse IgG #A4416 (Sigma-Aldrich) diluted 1:5000 in blocking buffer was added to each well and the plate incubated for 1 hr at room temperature with gentle agitation. Plates were washed 12 times in PBS-T. Wells were filled with 100 μL of SuperSignal ELISA Femto Maximum Sensitivity Substrate (Pierce) and incubated for 3 min at room temperature with gentle agitation. Luminescent counts were recorded using a Wallac Victor 2 Multilabel Counter (PerkinElmer Inc., Waltham, Mass.). The percentage inhibition of binding was calculated by the formula $(1-B/B_0) \times 100$, where B=luminescent counts at each concentration of fusion peptide in solution and $B_0$=luminescent counts at 0 μg/mL fusion peptide in solution.

e. Phage Display

The Ph.D.-C7C Phage Display Peptide Library Kit (New England BioLabs) was used to pan against 60 mm polystyrene dishes coated with antibody F1-40, to identify peptide ligands to F1-40, according to manufacturer's instructions. The M13 phage displays a randomized amino acid heptamer between two cysteine residues on the pIII minor coat protein. The cysteine residues form a disulphide bond, resulting in the heptamer being presented as constrained loop. Four series of panning and three phage amplification stages were carried out, prior to the growth and sequencing of individual plaques of the phage. A total of twelve clonal plaques from the 4$^{th}$ pan were picked for sequencing.

f. Cloning and Sequencing of Antibody Variable Regions

The method used here for the cloning and sequencing of variable regions for antibody heavy and light chains is based upon the method described fully in Current Protocols in Immunology (Morrison, 2002). Significant changes from this methodology are described here.

Hybridoma cells for F1-40 production were grown as previously described (Stanker et al., 2008). Culture volumes of 5 mL were centrifuged at 12000×g for 1 min to collect the cells. mRNA was purified from the cells using Trizol Reagent (Invitrogen), according to manufacturer's instructions. cDNA was transcribed into mRNA using primers H-chainR and L-chainR, and AMV reverse transcriptase according to manufacturer's instructions (Promega, Madison, Wis.) The cDNA was amplified by PCR using Phusion DNA polymerase and the appropriate pairs of primers (H-chain R and F3; L-chain R and F3). The cDNA was gel purified, then treated using the MasterTaq Kit (Eppendorf North America, Westbury, N.Y.) according to manufacturer's instructions to add A-overhangs to the DNA. The cDNA was then cloned into plasmid pCR4-TOPO, and transformed into TOP10 cells. Six individual colonies of *E. coli* harboring pCR4-H-chain and pCR4-L-chain were picked, grown and prepared for sequencing as described earlier.

g. Computer Tools

All DNA and amino acid sequence analysis was carried out using the tools of the Biology Workbench, Version 3.2 (San Diego Supercomputer Center, University of California, San Diego, Calif.). The three-dimensional diagrams of BoNT/A were generated using the crystal structure of BoNT/A (Lacy et al., 1998) manipulated with the MBT Protein Workshop (RCSB Protein Data Bank).

Binding of F1-40 to Peptide Fragments of the BoNT/A Light Chain

Figure 18:
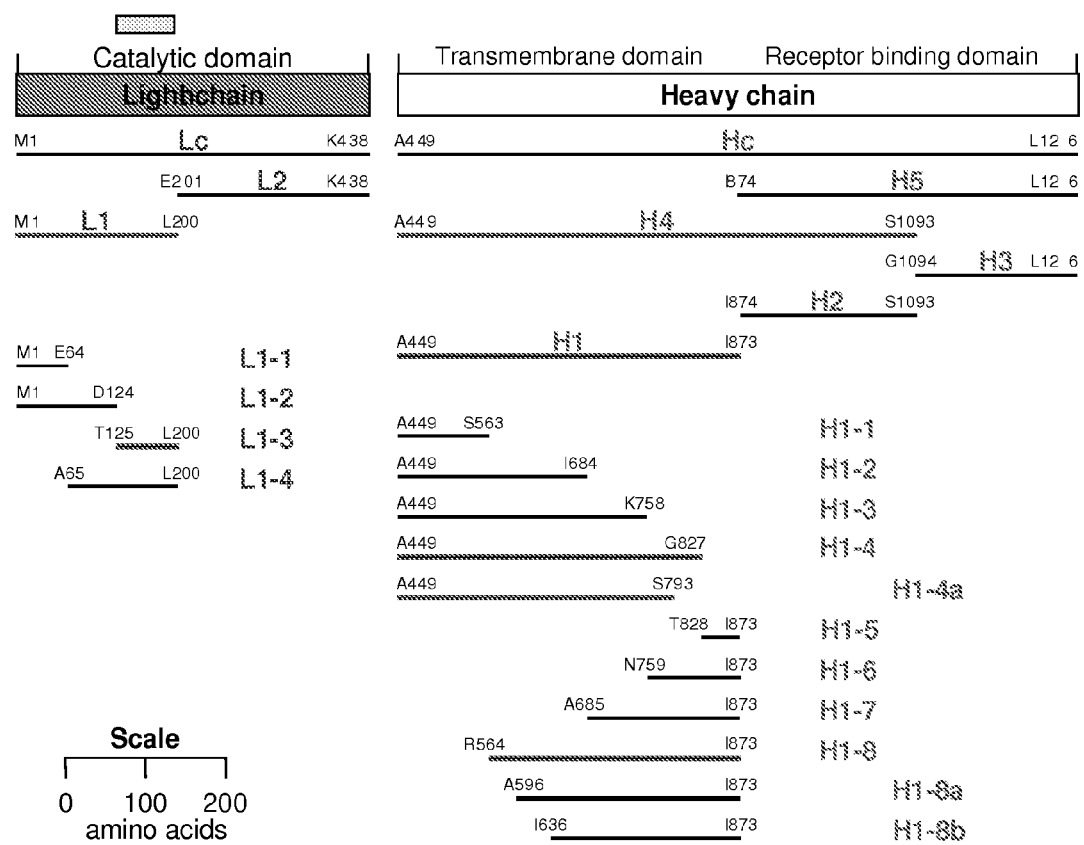
FIG. 18 is a diagram of recombinant BoNT/A peptides.

Seven recombinant peptide fragments of BoNT/A light chain (Lc, L1, L2, L1-1, L1-2, L1-3, L1-4) are shown in FIG. 18. These recombinant peptides were expressed as fusions to glutathione-S-transferase (GST). The relative molecular weights (rMW) of these recombinant peptide-GST proteins, observed by SDS-PAGE and silver staining, are shown in FIG. 2, panels A and C. In each case, the rMW corresponds to that predicted for the recombinant peptide-GST protein. Results from the Western blot analysis are shown in panels B and D. Clearly, F1-40 bound to fragments Lc and L1, but binding to L2 could not be detected. The L1 peptide fragment corresponds to amino acids M1 to L200. This region was subdivided by generating recombinant peptide fragments L1-1 through L1-4. In western blotting experiments mAb F1-40 was observed to bind only two of these recombinant peptide fragments, L1-3 and L1-4. In contrast, binding to L1-1 and L1-2 was not detected. These western blotting results, in particular antibody binding to L1-3, suggests that the epitope for F1-40 resides between amino acids T125 and L200.

Heptamer Peptide Ligands for F1-40 Identified by Phage Display

In an effort to further confirm that the epitope for F1-40 lies between amino acids T125 and L200, binding to a random phage display library was evaluated. Of the twelve clonal plaques picked for sequencing, one plaque failed to yield sequence, and the remaining eleven sequences of the heptamer peptide ligands for F1-40 are shown, with their frequency of occurrence, in Table 3. The most common motif, SSAFYPK, found in eight of the eleven plaques sequenced, did not readily map to a putative epitope region on the L1-3 peptide fragment, or to any other region on the light chain of BoNT/A. In contrast, motif QPDRS, common to the remaining three heptamer sequences from the phage display experiment, was similar to a region located within fragment L1-3 on the BoNT/A light chain (Table 4). Furthermore, the amino acids of this sequence QPDRS are brought into close proximity to each other by the tertiary structure of the toxin.

TABLE 3

Amino acid sequences identified using phage display against F1-40. The sequences of the heptamer peptide ligands to mAb F 1-40 were identified using the Ph.D.-C7C Phage Display Peptide Library Kit (New England BioLabs Inc.) to pan against mAb F1-40. Twelve clonal phage plaques were sequenced, one failed to yield sequence, and the frequency of the heptamer sequences observed is shown.

| Heptamer sequence | | | | | | | Frequency |
|---|---|---|---|---|---|---|---|
| S | S | A | F | Y | P | K | 8 |
| T | R | Q | P | D | R | S | 1 |
| T | L | Q | P | D | R | S | 1 |
| S | L | Q | P | D | R | S | 1 |

TABLE 4

Mutations made in the putative F1-40 epitope rehion on plasmid pGS-Lc.
All four vectors shown above harbored and expressed the entire BoNT/A light chain (P-1 to K-438), but only the mutated region (T-125 to Q-162) is shown here. All other amino acids within the light chain were not mutated. Dashes indicate that amino acids have been deleted. Single amino acid mutations are indicated in gray shading.

| Vector | Light chain, from T-125 to Q-162 | SEQ ID NO: |
|---|---|---|
| pGS-Lc | TELKVIDTNCINVIQPDGSYRSEELNLVIIGPSADIIQ | SEQ ID NO: 30 |
| pGS-Lc-Δ | TELKVIDTN---------------LNLVIIGPSADIIQ | SEQ ID NO: 31 |
| pGS-Lc-QPD | TELKVIDTNCINVIGGGGSYRSEELNLVIIGPSADIIQ | SEQ ID NO: 32 |
| pGS-Lc-RS | TELKVIDTNCINVIGGGGSYGGEELNLVIIGPSADIIQ | SEQ ID NO: 33 |

Binding of F1-40 to Mutants of the Lc Peptide Fragment

We developed mutant recombinant Lc peptides carrying specific amino acid deletions or substitutions within the region identified via phage display (Table 3). The region spanning from C134 to E148 forms a looped structure, and the entire loop was deleted from the recombinant peptide Lc to form mutant peptide Lc-Δ. In mutant peptide Lc-QPD the amino acids Q139, P140 and D141 were all mutated to glycine. In mutant peptide Lc-RS the amino acids R145 and S146 were both mutated to glycine. Panel A in FIG. 19 shows a silver stained gel of the Lc peptide fragment and the three mutant peptides. As a control, a polyclonal anti-BoNT/A toxoid antiserum was used in a Western blot, which clearly bound the Lc peptide and all three mutant peptides (Panel B). Binding of F1-40 to these mutant peptides is shown by Western blot in Panel C. F1-40 bound peptides Lc and L-RS, but binding to Lc-Δ and to Lc-QPD was not detected. These data demonstrate that the mutation of the QPD motif to GGG decreases F1-40 binding to the Lc peptide to a level which cannot be detected under these conditions.

Competition ELISA

Competition ELISA assays were performed to better quantify the differences of antibody binding to the mutant peptides observed in the above Western blotting experiments. Results from these experiments are shown in FIG. 4. Peptide Lc was the most effective at competing binding of F1-40 to immobilized Lc, with 50% inhibition achieved at a concentration of ~3.5 µg/mL. Mutant peptide Lc-RS was the next most effective competitor resulting in 50% inhibition of control activity at a concentration of ~24 µg/mL, roughly 7-fold higher than that observed for the recombinant Lc peptide. Mutants Lc-Δ and Lc-QPD did not compete for F1-40 under these conditions even at the highest concentration of peptide used (60 µg/mL).

F1-40 Heavy and Light Chain Variable Region Sequences

Figure 5:
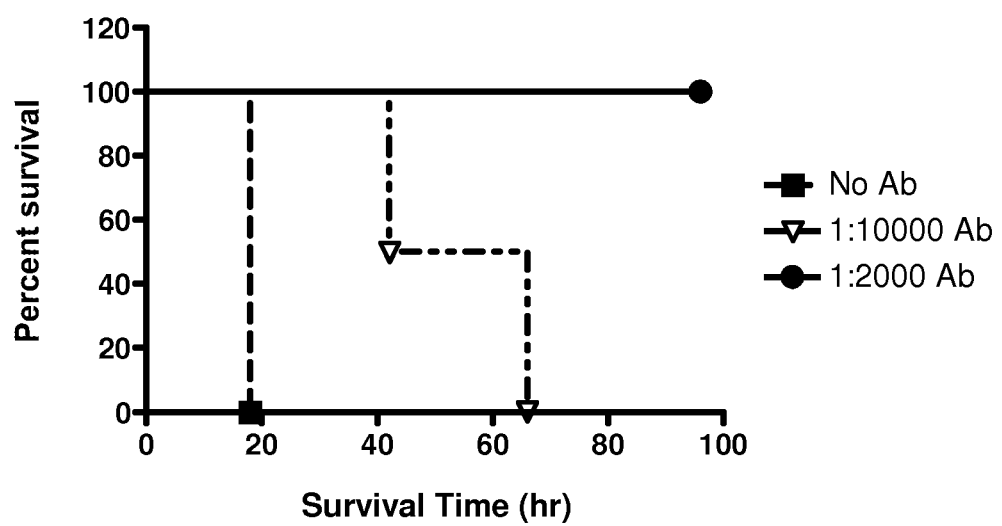
FIG. 5 is a plot of the Mouse Protection Assay for F1 2-13-48 Ascites (from 30 pgBoNT/A/mouse).

The cDNA sequences of the heavy and light chain variable regions for F1-40 are shown in FIG. 5. The nucleotide sequence of the entire cloned regions is shown, with the corresponding amino acids shown from the start of the leader peptide to the end of the fourth framework region of each chain. The leader sequences, framework regions, complementarity determining regions (CDRs) and J-regions were identified by inspecting the alignment of the F1-40 heavy and light chains to other antibody sequences (Wood & Coleclough, 1984; Recinos et al., 1994, 1995; Morrison, 2002; Livesay & Subramaniam, 2004). The nucleotide sequence reported was identical across the six individual colonies of *E. coli* harboring either pCR4-L-chain or pCR4-H-chain that were analyzed.

Figure 6:
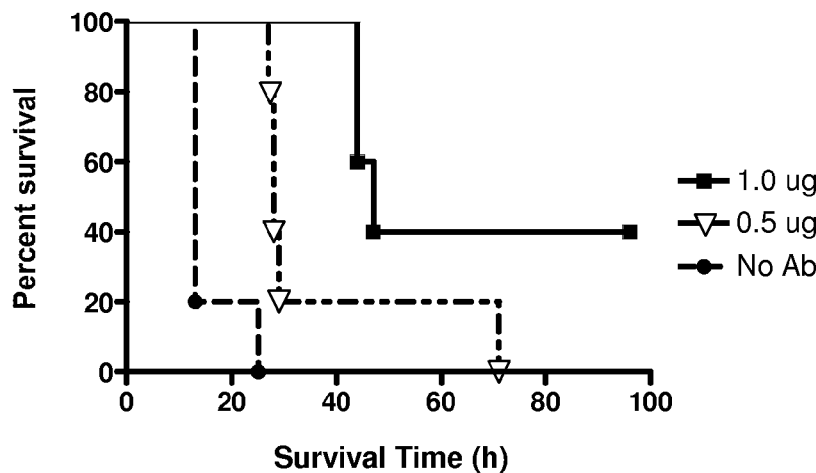
FIG. 6 is a plot of mice protected with F1 2-13-8 challenged with 40 pg BoNT/A (150 kDa) and 160 pg BoNT/A (900 kDa) respectively.
Figure 6:
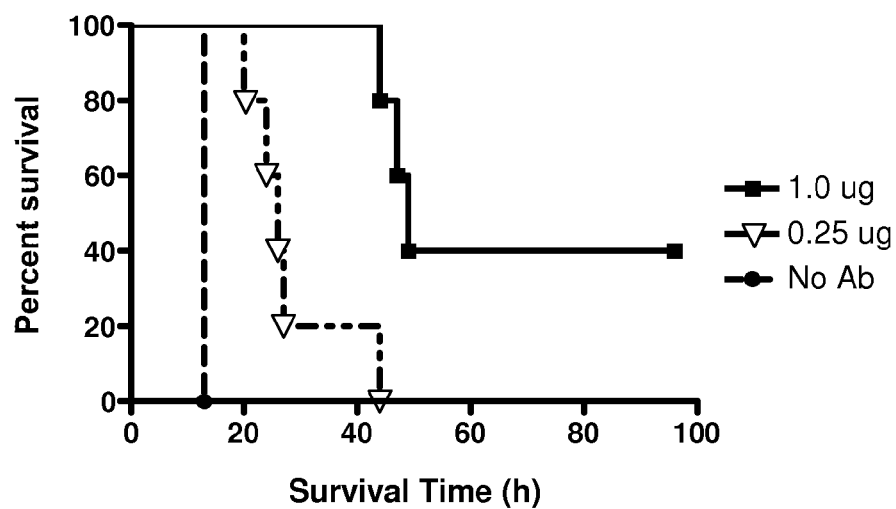
Figure 7:
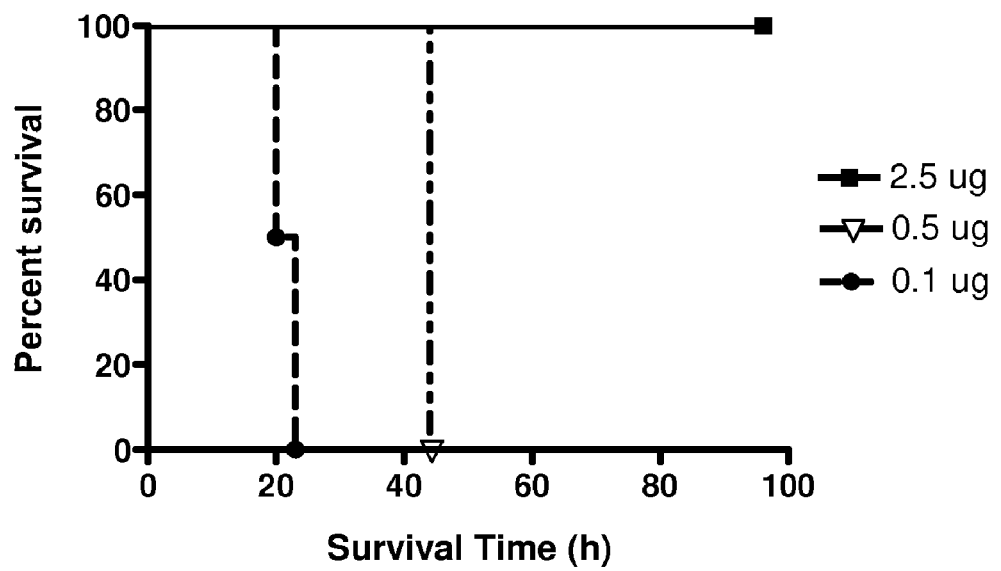
FIG. 7 is a plot of mice protected with F1 5-3-12 challenged with 40 pg BoNT/A (150 kDa) and 160 pg BoNT/A (900 kDa) respectively.
Figure 7:
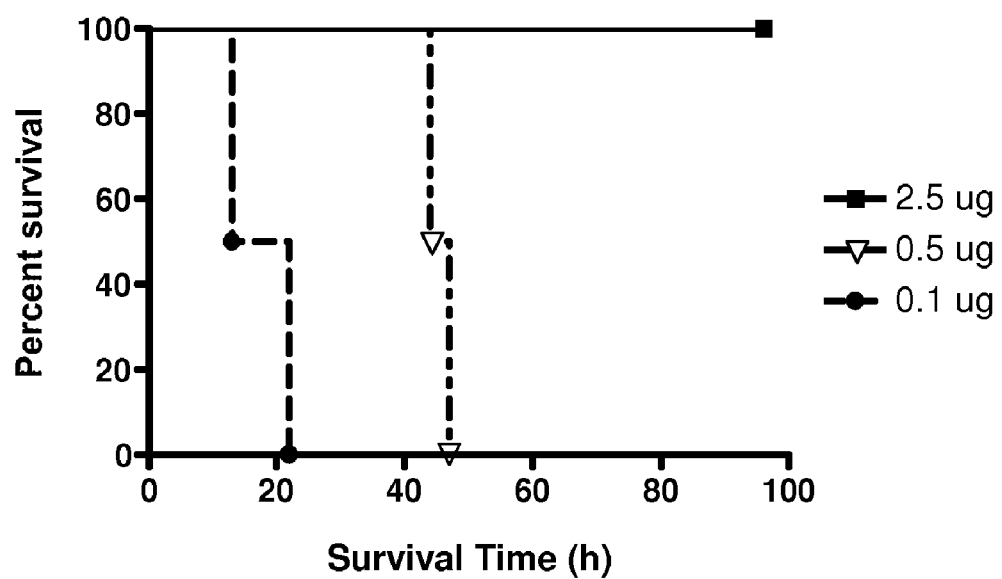
Figure 8:
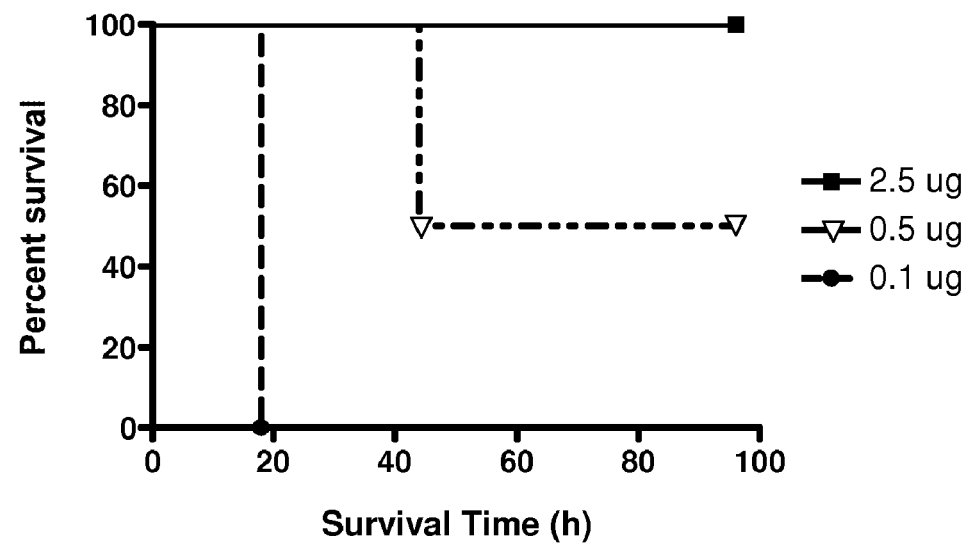
FIG. 8 is a plot of mice protected with F1 40-12-8 challenged with 40 pg BoNT/A (150 kDa) and 160 pg BoNT/A (900 kDa) respectively.
Figure 8:
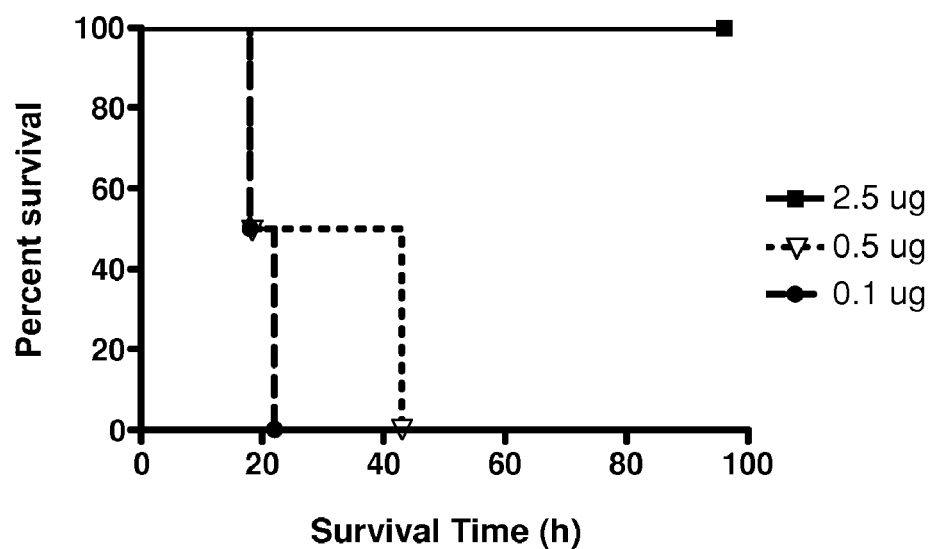
Figure 9:
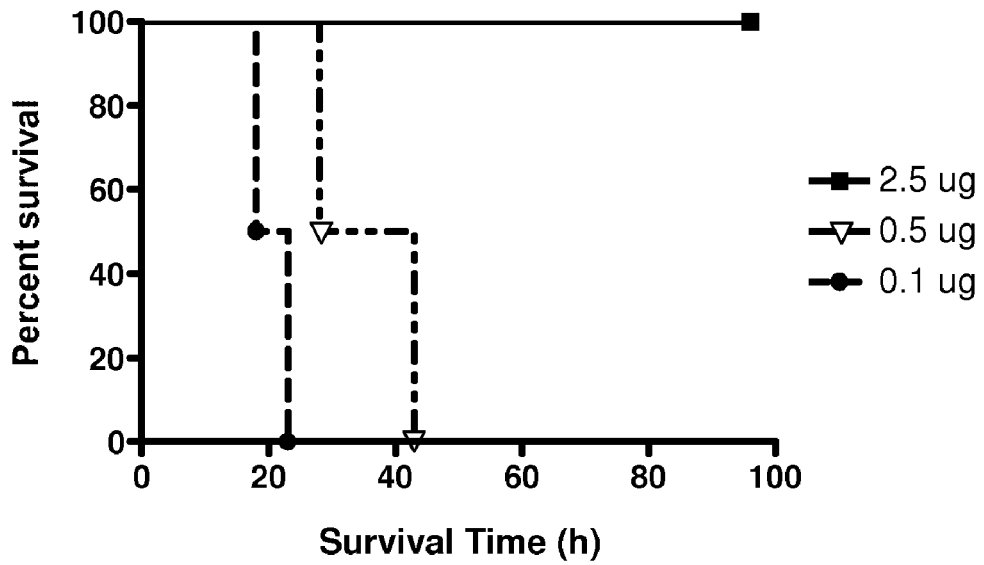
FIG. 9 is a plot of mice protected with F1 43-12-8 challenged with 40 pg BoNT/A (150 kDa) and 160 pg BoNT/A (900 kDa) respectively.
Figure 9:
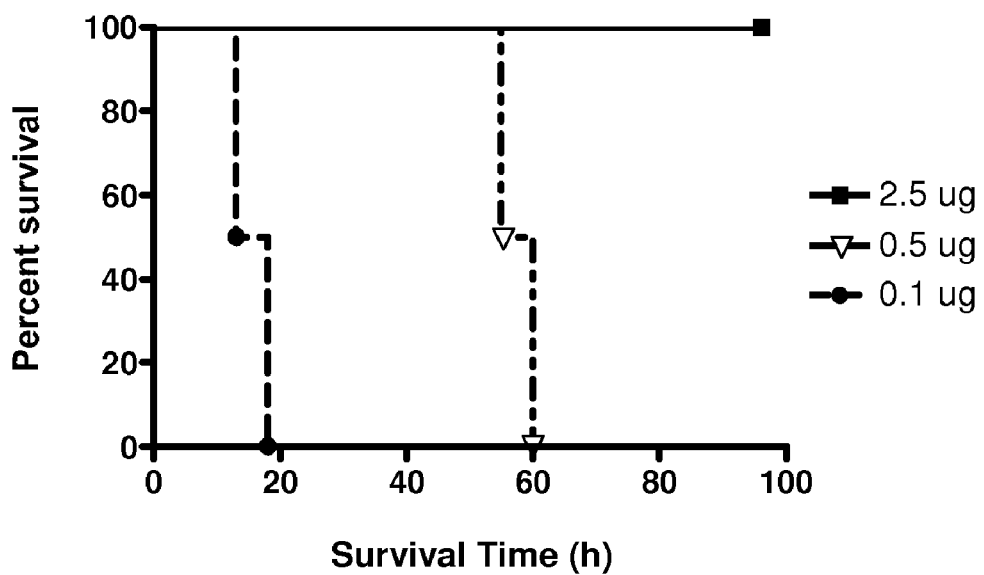
Figure 10:
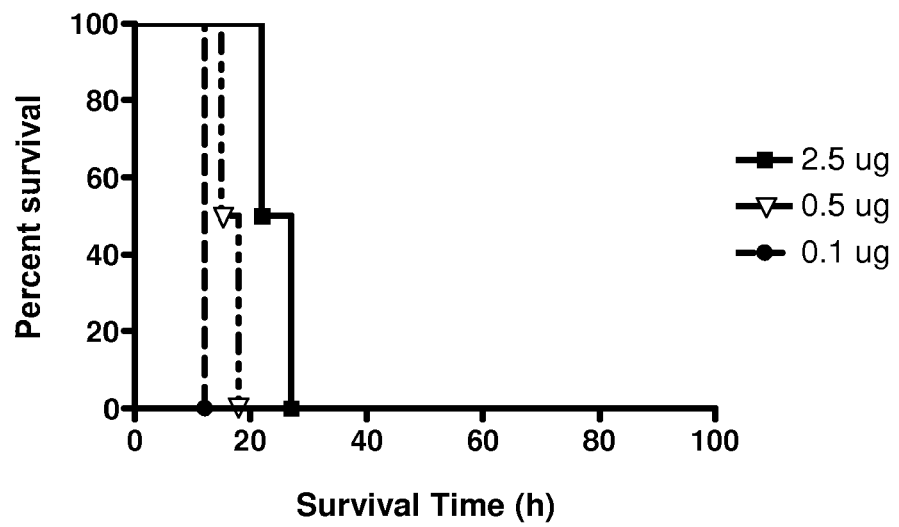
FIG. 10 a plot of mice protected with F2 46 challenged with 40 pg BoNT/A (150 kDa) and 160 pg BoNT/A (900 kDa) respectively.
Figure 10:
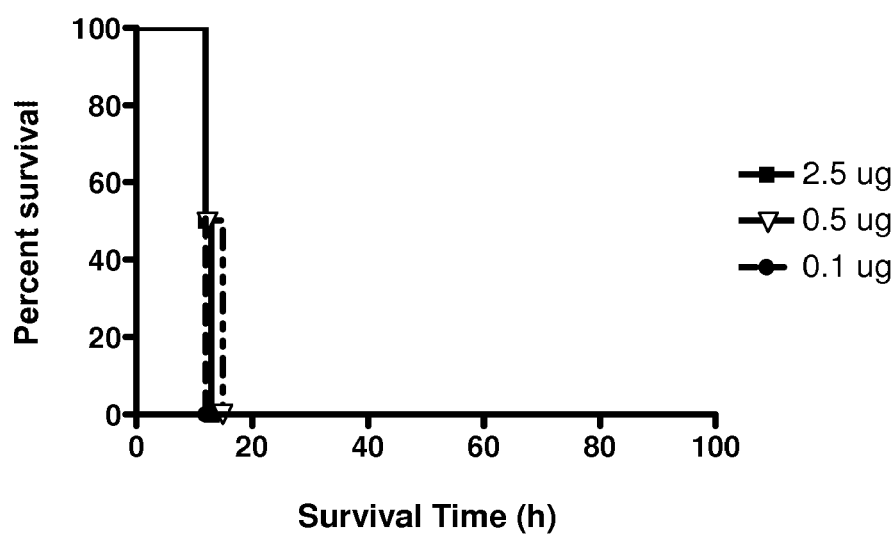
Figure 11:
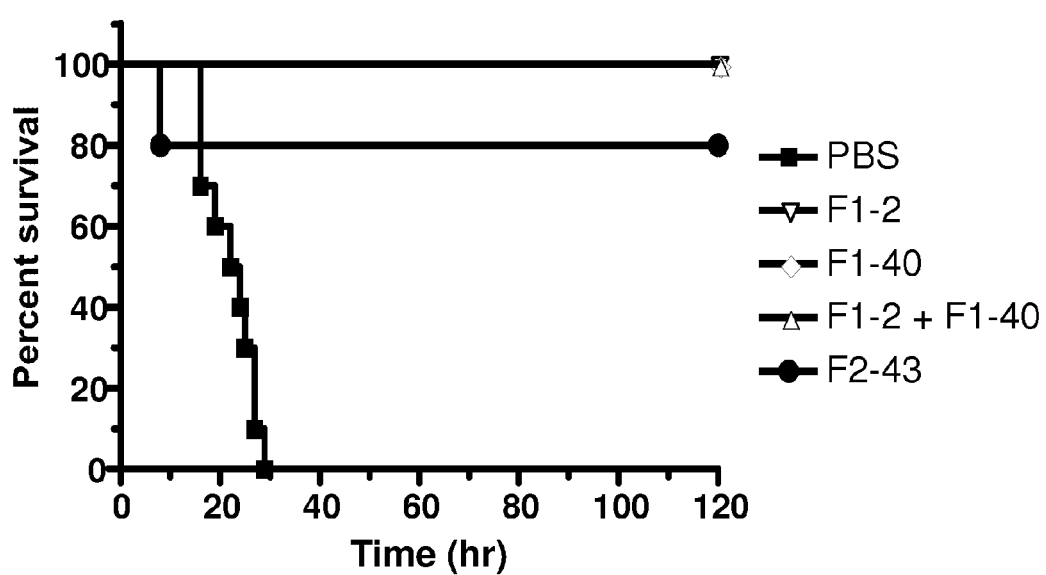
FIG. 11 is a plot of antibody rescue mice orally intoxicated with 4 ug of complex BoNT/A. F1-2+F1-40 combo.
Figure 12:
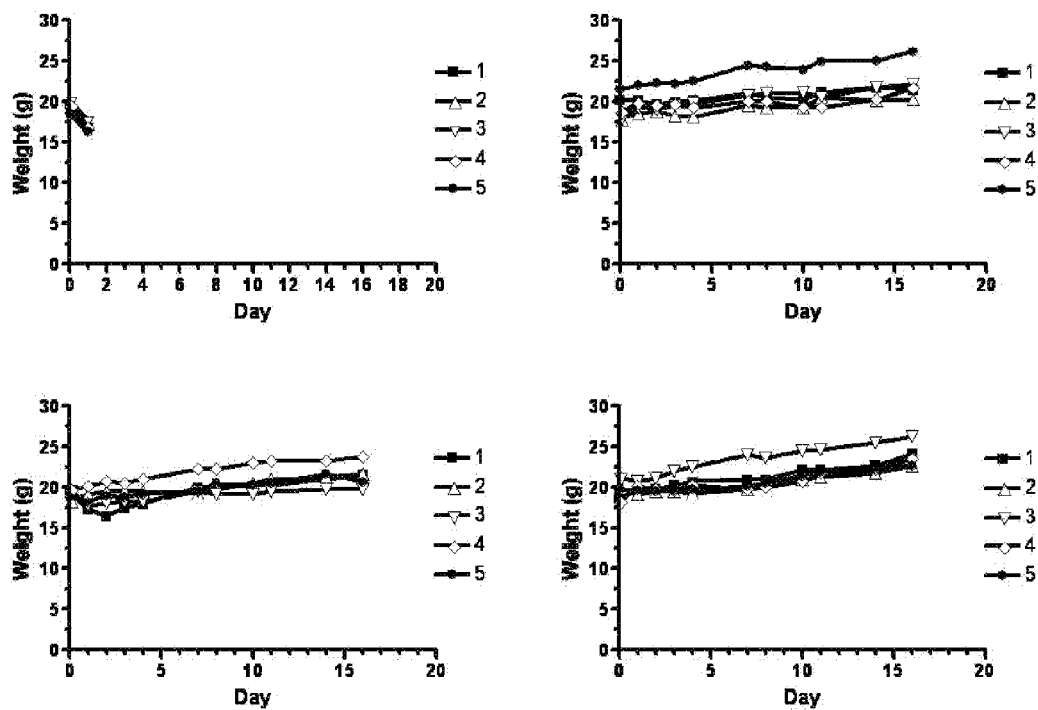
FIG. 12 is a plot of antibody rescue mice orally intoxicated with 4 ug of complex BoNT/A (PBS; F1-2; F1-40; F1-2+ F140).
Figure 13:
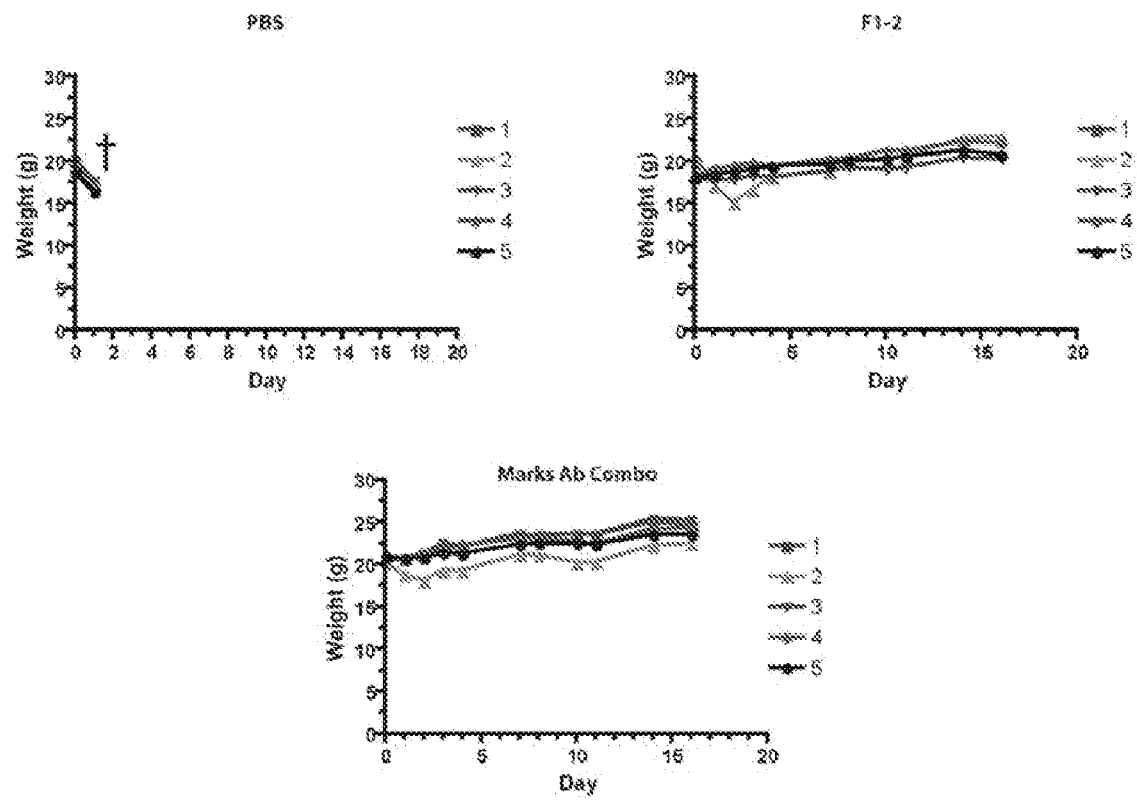
FIG. 13 is a plot of antibody rescue mice orally intoxicated with 4 ug of complex BoNT/A (PBS; F2-43; F1-2; F1-40; F1-2+F-140).
Figure 15:
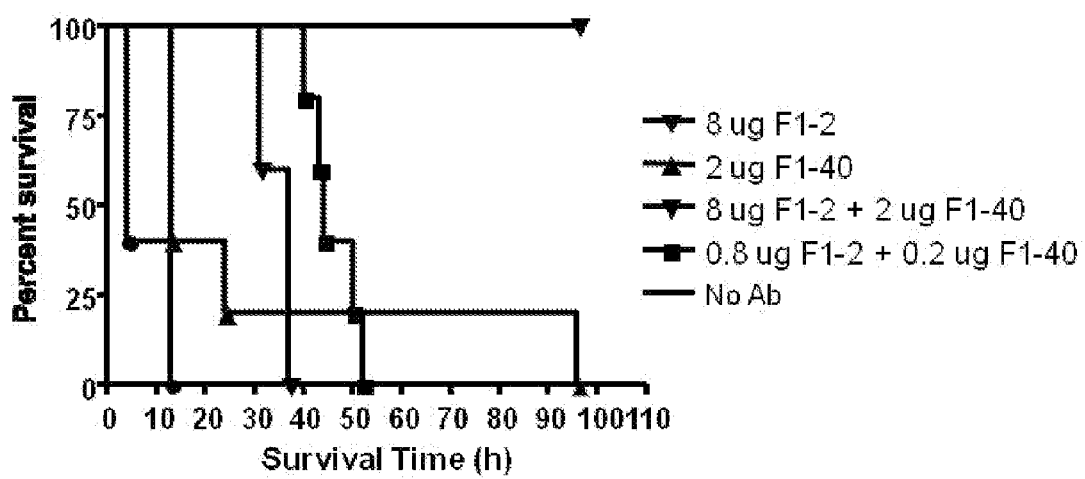
FIG. 15 is a plot of the additive protection from mAbs against two different epitopes.
Figure 16:
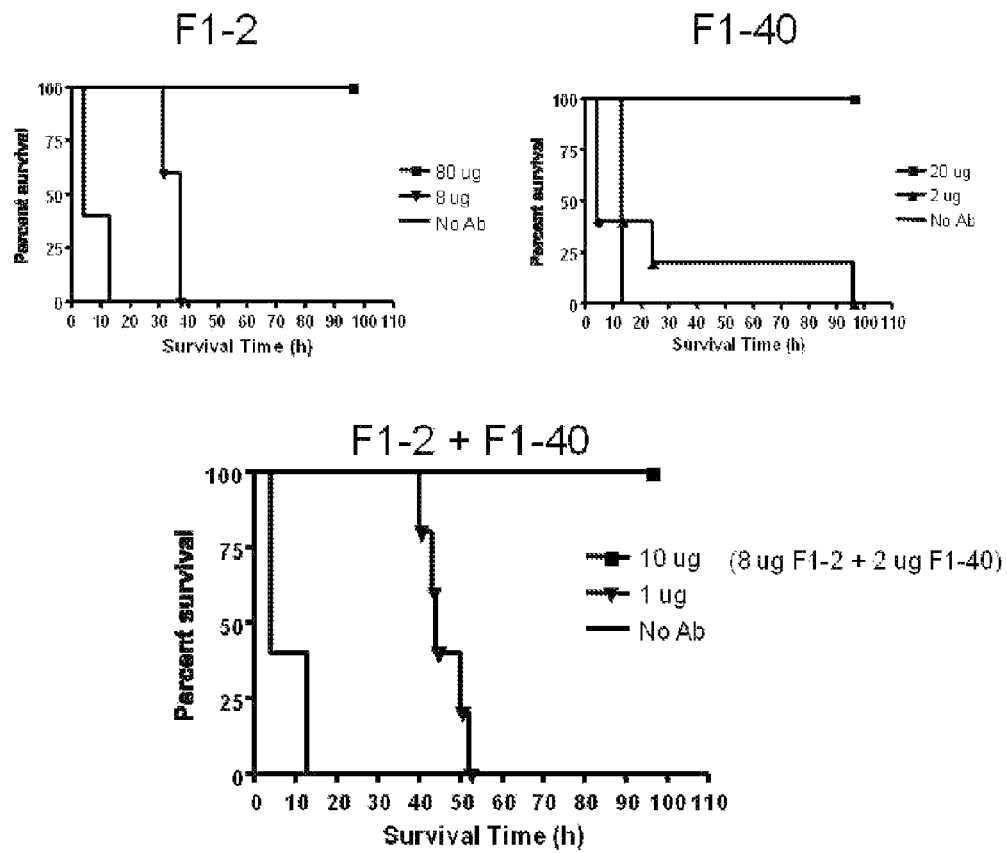
FIG. 16 is a plot of Mouse protection from 50 $LD_{50}$ BoNT/A holotoxin with mAbs.
Figure 17:
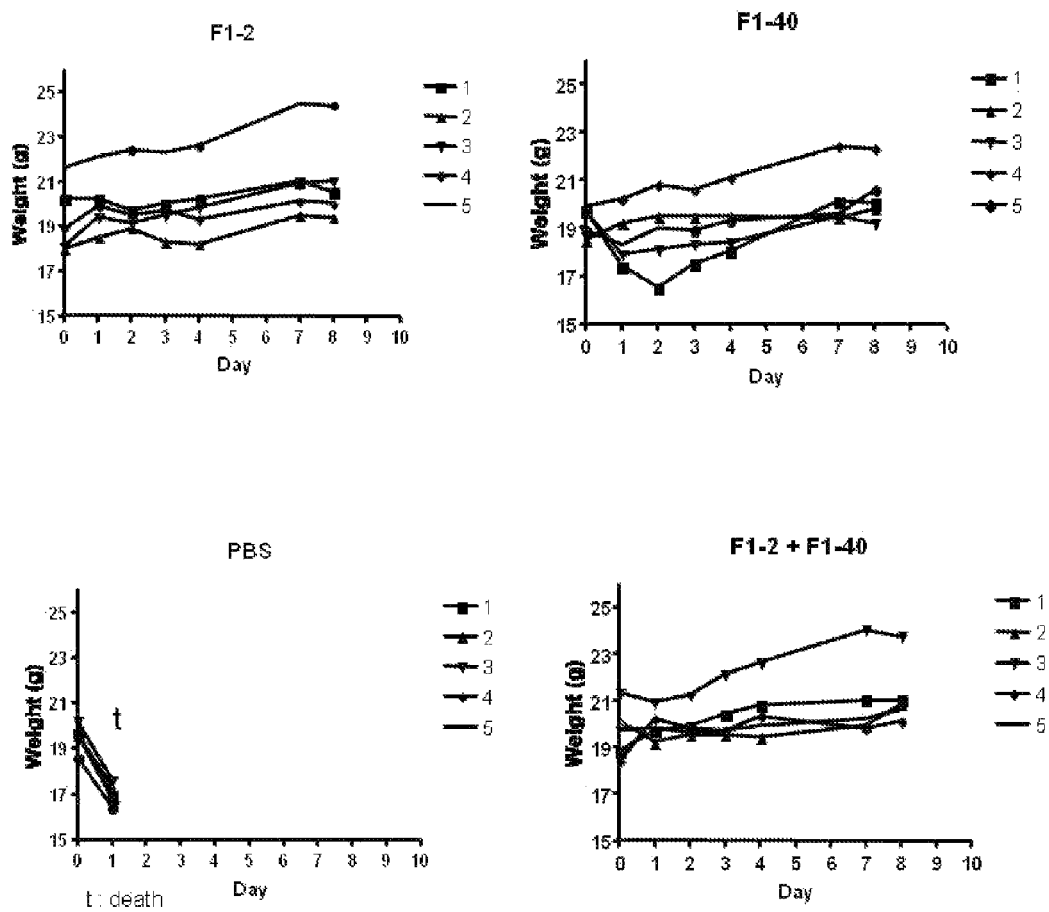
FIG. 17 is a plot of the rescue of 4 μg BoNT/A ig treated mice with mAb by iv.

The epitope of mAb F1-40 was mapped to a five amino acid motif, QPDRS, SEQ ID NO:38 on the light chain of BoNT/A. Initial experiments measuring antibody binding by Western blots to recombinant peptide fragments of toxin light chain showed that the F1-40 epitope was contained within a 76 amino acids region from T125 to L200. Phage display experiments suggested that a peptide ligand containing the amino acid motif QPDRS, SEQ ID NO:38 might constitute part or all of the F1-40 epitope. When these amino acids were mapped onto the three-dimensional crystal structure of BoNT/A, they formed a compact, almost continuous sequence, as shown in FIG. 6 (Lacy et al., 1998). Although R145 and S146 are separated from Q139, P140 and D141 by three intervening amino acids, the BoNT/A tertiary structure brings them into close proximity, forming an exposed loop on the light chain of the toxin. Replacement of R145 and S146 with glycine residues had no obvious effect on F1-40 binding as illustrated by Western blot, but competition ELISA experiments revealed a 7-fold decrease in the relative affinity of mutant Lc-RS for F1-40 compared to the recombinant Lc peptide. These data suggest that R145 and S146 contribute significantly to the binding of F1-40 to the light chain of BoNT/A, since the mutation of these residues to glycines is insufficient to abolish binding. Mutation of Q139, P140 and D141 to glycine residues abolished binding of F1-40 to the Lc peptide in both the competition ELISA and western blotting experiments, suggesting that the QPD triad is necessary for the binding of F1-40 to the light chain of BoNT/A. The ELISA data is consistent with our observation that F1-40 did not bind mutant peptides Lc-Δ and Lc-QPD by Western blotting.

The QPD motif forms a short loop on the surface of the BoNT/A holotoxin, with all three amino acids exposed to solvent (FIG. 6). We have previously shown that binding of F1-40 to BoNTs B through G is undetectable by ELISA (Stanker et al., 2008). Analysis of the amino acid sequence and three-dimensional structure of the light chain of BoNTs B through G reveals that although a loop is formed in a similar position on the light chain in all other BoNT types (except BoNT/C—there is no crystal structure available), none possess the QPD motif in its entirety (Eswaramoorthy & Swaminathan, 2000; Agarwal et al., 2004, 2005; Arndt et al., 2005, 2006). It is highly probably that inability of F1-40 to bind the other serotypes of BoNT is due to the absence of a complete QPD motif. Interestingly, BoNT/G possesses Q139 and P140 but not D141, yet it remains unable to bind F1-40, leading to speculation about the possible role that D141 might play in determining the specificity of F1-40 to BoNT/A (Stanker et al., 2008; Arndt et al., 2005). It is possible that other amino acids not examined in this study may also contribute significantly to the binding of F1-40 to the light chain of BoNT/A.

Using a series of overlapping synthetic peptides, Dolimbek et al. (2008) successfully mapped continuous regions of BoNT/B recognized by antibodies derived from human, horse and mouse. Whilst this is an established technique, it only detects linear epitopes and overlooks conformational epitopes. We expect our experimental approach, of employing larger recombinant GST-fusion peptides for Western blots in combination with analysis of antibody binding to a phage display library, to increase the likelihood of identifying potential conformational epitopes of other antibodies in the future.

Although the phage display analysis yielded the sequence QPDRS, SEQ ID NO:38 it also provided the anomalous motif SSAFYPK, SEQ ID NO:34 in eight of the eleven sequenced plaques. Unlike the sequence QPDRS, SEQ ID NO:38 this second sequence could not be mapped onto the light chain of BoNT/A, and it probably represents a mimotope of the F1-40 epitope. Mimotopes are commonly identified by phage display, and this faculty has been widely exploited to generate potential peptide vaccine candidates (Hill & Stockley, 1996; Manoutcharian et al., 2001). When using phage display to search for an epitope, multiple mimotopes that bind a monoclonal antibody can be selected, and it is necessary to examine every mimotope to identify an epitope region (Li at al., 2007; 2008). Supporting evidence defining an epitope, such as the Lc peptide mutagenesis data presented in this study, must be included in the analysis before assigning an epitope to an antibody. The assignment of an epitope motif to F1-40 including Q139, P140, D141, R145 and S146 is consistent with the BoNT serotype A specificity of F1-40.

Sequence analysis of the cDNA derived from the mRNA coding for the heavy and light chains of F1-40 reveals features that are typical of mouse monoclonals antibodies (Kabat et al., 1987; Recinos et al., 1994; Livesay & Subramaniam, 2004). On the k-light chain, the section GVDGDIVMTQ SEQ ID NO:39 from G29 to Q38 is a repeat of a preceding section from G17 to Q26, and forms the junction between the leader sequence and first framework region of the mature light chain. This repeat is not always present in k-light chains. The J-region of the heavy chain, TLVTVSA SEQ ID NO:40, is type 3 and the J-region of the k-light chain, TKLEIK SEQ ID NO:41, is type 2 (Wood and Coleclough, 1984).

We have characterized in detail the epitope of anti-BoNT/A mAb F1-40, and have cloned and sequenced the variable and J-regions of the antibody's heavy and light chains. This information not only provides important insight into the nature of the interaction between F1-40 and BoNT/A, but also is essential for the future development of F1-40 as an integral component of a test for BoNT/A contamination of food.

TABLE 5

Antibody sequences (Nucleic Acid and Protein)-Shaded = Complementary Determining Region (CDR) CDR-1, CDR,-2, CDR-3 and Framework Regions.

F1-40 Heavy Chain Protein Sequence.

SEQ ID NO: 1

Leader

```
atggctgtcttggggctgctcttctgcctgttgacattcccaagctgtgtcctgtcccag
 M   A   V   L   G   L   L   F   C   L   L   T   F   P   S   C   V   L   S   Q
```

Framework Region-1

```
gtgcagctgaaggaatcaggacctggcctggtggcgccctcacagagcctgtccatcaca
 V   Q   L   K   E   S   G   P   G   L   V   A   P   S   Q   S   L   S   I   T
```

CDR-1 | Framework

```
tgcactgtctcagggctctcattaaccaactatggtgtaagctgggttcgccagcctcca
 C   T   V   S   G   L   S   L   ░░░░░░░░░░░░   W   V   R   Q   P   P
```

Region-2 | CDR-2

```
ggaaagggactggagtggctgggaataatttggggtgacggaagcacaagttatcattca
 G   K   G   L   E   W   L   G   ░░░░░░░░░░░░░░░░░░░░░░░░░
```

TABLE 5-continued

Antibody sequences (Nucleic Acid and Protein)-Shaded = Complementary Determining Region (CDR) CDR-1, CDR,-2, CDR-3 and Framework Regions.

```
_____|_____Framework Region-3_____
gctctcacatccagattgagcatcagtaaggataactccaagagccaagttttcttaaca
             R  L  S  I  S  K  D  N  S  K  S  Q  V  F  L  T
```

```
_____|__CDR-3_____
ctgaacagtctgcaaactgatgacacagccacgtactactgtgccaccgcctactatggg
L  N  S  L  Q  T  D  D  T  A  T  Y  Y  C  A  T
```

```
_____|_____Framework Region-4_____|
tacaccctgtttgcttactggggccaagggactctggtcactgtctctgca
                  W  G  Q  G  T  L  V  T  V  S  A
```

F1-40 Light Chain Sequence.

SEQ ID NO: 2

```
|_____Leader_____|_
atggagtcacagactcaggtctttgtattcgtgtttctctggttgtctggtgttgacgga
M  E  S  Q  T  Q  V  F  V  F  V  F  L  W  L  S  G  V  D  G
```

```
_____Framework-1 Region_____
atggagtcacagactcaggtctttgtattcgtgtttctctggttgtctggtgttgacgga
M  E  S  Q  T  Q  V  F  V  F  V  F  L  W  L  S  G  V  D  G
```

```
_____Framework Region-1 (cont.)_____|__CDR-1_____
aaattcatgtccacatcagtaggagacagggtcagcatcacctgcaaggccagtcaggat
K  F  M  S  T  S  V  G  D  R  V  S  I  T  C
```

```
_CDR-1 (cont.)_|_____Framework Region-2_____|
gtgagtactactgtggcctggtatcagcagaaaccagggcaatctcctaaactactgatt
                W  Y  Q  Q  K  P  G  Q  S  P  K  L  L  I
```

```
____|____CDR-2_____|_____Framework Region-3_____
tattcggcatcctaccggtacactggagtccctgatcgcttcactggcagtggatctggg
Y                    T  G  V  P  D  R  F  T  G  S  G  S  G
```

```
_____ Framework Region-3 (cont.)_____|
acggatttcactttcaccatcagcagtgtgcaggctgaagacctggcagtttattactgt
T  D  F  T  F  T  I  S  S  V  Q  A  E  D  L  A  V  Y  Y  C
```

```
_|_____CDR-3_____|_____Framework Region-4____|
cagcaacattatagtactcctcccacgttcggaggggggaccaagctggaaataaaa
Q  Q  H  Y  S  T  P  P  T  F  G  G  G  T  K  L  E  I  K
```

F2-43 Light Chain Variable Region Sequence.

SEQ ID NO: 3

```
|_____Leader_____|__
atggagtcacagactcaggtctttgtattcgtgtttctctggttgtctggtgttgacgga
M  E  S  Q  T  Q  V  F  V  F  V  F  L  W  L  S  G  V  D  G
```

```
____ Framework Region-1_____
gacattgtgatgacccagtttgcaggtgttgacggagacattgtgatgacccagtctcac
D  I  V  M  T  Q  F  A  G  V  D  G  D  I  V  M  T  Q  S  H
```

```
_____|__CDR-1_____
aaattcatgtccacatcagtaggagacagggtcagcatcacctgcaaggccagtcaggat
K  F  M  S  T  S  V  G  D  R  V  S  I  T  C
```

TABLE 5-continued

Antibody sequences (Nucleic Acid and Protein)-Shaded = Complementary
Determining Region (CDR) CDR-1, CDR,-2, CDR-3 and Framework Regions.

|__CDR-1 (cont.)_|_____Framework Region-2_____|
gtgagtactactgtggcctggtatcagcagaaaccagggcaatctcctaaactactgatt
░░░░░░░░░░ W Y Q Q K P G Q S P K L L I ___|____CDR-2_____|_____Framework Region-3_____
tattcggcatcctaccggtacactggagtccctgatcgcttcactggcagtggatctggg
Y ░░░░░░░░░ T G V P D R F T G S G S G _____Framework Region-3 (cont.)_____
acggatttcactttcaccatcagcagtgtgcaggctgaagacctggcagtttattactgt
T D F T F T I S S V Q A E D L A V Y Y C _|_____CDR-3_____|_____Framework Region-4_____|
cagcaacattatagtactcctcccacgttcggaggggggaccaagctggaaataaaa
░░░░░░░░░░░ F G G G T K L E I K F1-2 Heavy Chain V-region sequences.

SEQ ID NO: 4

_____Leader_____|_____
atgaacttcgggttgagcttggttttccttgtccttgttttaaaaggtgtccagtgtgaa
M N F G L S L V F L V L V L K G V Q C E gtgatgttggtggagtctggggggaggcttagtgaaacctggagggtccctggaactctcc
V M L V E S G G G L V K P G G S L E L S _____Framework Region-1__|____CDR-1_____|_Framework Region-2_
tgtattgcctctggattccacttcagttcctatgccatgtcttgggttcgccagactccg
C I A S G F T F ░░░░░░░ S W V R Q T P _____|_____CDR-2_____
gaaaagaggctggagtgggtcgcagccattgatagtggtggttattacacctactatcca
E K R L E W V A ░░░░░░░░░░░░░░

_____|_____Framework Region-3_____
gacaatgtgaagggccgattcaccatctccagagacaatgccaagaacaccctgtacctg
░░░░░░░ R F T I S R D N A K N T L Y L _____|__CDR-3_
caaatgaacagtctgaggtctgaggacacggccatatattactgtacaagacagggaca
Q M N S L R S E D T A I Y Y C T R ░░░░

_____|_____ Framework Region-4_____
cgggtctcctataggtacgtccttgactactggggccaaggcaccactctctcagtctcc
░░░░░░░░░░░░░ W G Q G T T L S V S _____|
tcagcc
S A F1-2 Light Chain V-region Sequence.

SEQ ID NO: 5

__Framework Region-1_____|__CDR-1_____|_FWR-
2_____
G D I V M T Q S H K F M S T S V G D R V S I T C ░░░░░░░░░ W Y Q Q K P G Q S P
K L

TABLE 5-continued

Antibody sequences (Nucleic Acid and Protein)-Shaded = Complementary
Determining Region (CDR) CDR-1, CDR,-2, CDR-3 and Framework Regions.

```
_____|_CDR-2_____|_____ Framework Region-
2_____|___
L I Y ▒▒▒▒▒▒▒▒▒▒▒▒) T G V P D R F T G S G S G T D F T F T I S S V Q A E D L A V Y Y C
▒▒
```

```
__CDR-3_____|_Frarmwork Region-4_|
▒▒▒▒▒▒▒▒▒▒▒▒▒▒▒▒ F G G G T K L E I K
```

What is claimed is:

1. An isolated and purified monoclonal antibody produced by the continuous hybridoma cell line having deposit accession number ATCC PTA-8336.

2. A composition comprising the monoclonal antibody of claim 1.

3. An isolated and purified monoclonal antibody produced by the continuous hybridoma cell line having deposit accession number ATCC PTA-8337.

4. A composition comprising the monoclonal antibody of claim 3.

5. An isolated and purified monoclonal antibody produced by the continuous hybridoma cell line having deposit accession number ATCC PTA-8338.

6. A composition comprising the monoclonal antibody of claim 5.

7. A kit for detecting BoNT/A in a sample, said kit comprising: (1) a container comprising a monoclonal antibody selected from the group consisting of ATCC PTA-8336, ATCC PTA-8337, ATCC PTA-8338, ATCC PTA-8339, and mixtures thereof; and (2) instructions for using the antibody for the purpose of binding to BoNT/A to form an immunological complex and detecting the formation of the immunological complex such that presence or absence of immunological complex correlates with presence or absence of BoNT/A in said sample.

8. A method for detecting BoNT/A comprising (1) incubating a sample with the monoclonal antibody selected from the group consisting of ATTC PTA-8336, ATCC PTA-8337, ATCC PTA-8338, ATCC PTA-8339, and mixtures thereof; and (2) detecting the antibody-BoNT/A complex wherein the presence or absence of the complex indicates the presence or absence of BoNT/A in the sample.

9. A method for detecting BoNT/A according to claim 8 wherein said sample is aqueous, biological, environmental or a food product.

10. A method for capturing BoNT/A from a sample, said method comprising contacting said sample with the monoclonal of claims 1, 3 or 5, and isolating the complex formed between the BoNT/A in the sample and the monoclonal antibody.

* * * * *